(12) United States Patent
Denison et al.

(10) Patent No.: US 7,714,757 B2
(45) Date of Patent: May 11, 2010

(54) CHOPPER-STABILIZED ANALOG-TO-DIGITAL CONVERTER

(75) Inventors: Timothy J. Denison, Minneapolis, MN (US); Joel A. Anderson, Brooklyn Park, MN (US); Michael W. Heinks, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/861,939

(22) Filed: Sep. 26, 2007

(65) Prior Publication Data

US 2009/0079607 A1    Mar. 26, 2009

(51) Int. Cl.
*H03M 3/00* (2006.01)
(52) U.S. Cl. .................................. 341/143; 341/155
(58) Field of Classification Search ................. 341/143, 341/155
See application file for complete search history.

(56) References Cited

U.S. PATENT DOCUMENTS

| | | | |
|---|---|---|---|
| 3,130,373 | A | 4/1964 | Braymer |
| 3,273,141 | A | 9/1966 | Hackett |
| 4,177,819 | A | 12/1979 | Kofsky et al. |
| 4,188,586 | A | 2/1980 | Egami |
| 4,466,440 | A | 8/1984 | Money et al. |
| 4,912,423 | A | 3/1990 | Milkovic et al. |
| 4,933,642 | A | 6/1990 | Lee |
| 4,990,914 | A | 2/1991 | Giancarlo |
| 5,024,221 | A | 6/1991 | Morgan |
| 5,039,989 | A * | 8/1991 | Welland et al. ............. 341/143 |
| 5,061,593 | A | 10/1991 | Yoerger et al. |
| 5,068,659 | A * | 11/1991 | Sakaguchi .................. 341/143 |
| 5,068,660 | A | 11/1991 | Swanson et al. |
| 5,113,143 | A | 5/1992 | Wei |
| 5,179,947 | A | 1/1993 | Meyerson et al. |

(Continued)

FOREIGN PATENT DOCUMENTS

EP    0 354 060    2/1990

(Continued)

OTHER PUBLICATIONS

Enz et al., "Circuit techniques for reducing the effects of op-amp imperfections: autozeroing, correlated double sampling, and chopperstabilization," Proceedings of the IEEE, vol. 84, No. 11, pp. 1584-1614, Nov. 1996.

(Continued)

*Primary Examiner*—Khai M Nguyen
(74) *Attorney, Agent, or Firm*—Shumaker & Sieffert, P.A.

(57) ABSTRACT

This disclosure describes a chopper-stabilized sigma-delta analog-to-digital converter (ADC). The ADC is configured to provide accurate output at low frequency with relatively low power. The chopper-stabilized ADC substantially reduces or eliminates noise and offset from an output signal produced by the mixer amplifier. Dynamic limitations, i.e., glitching that result from chopper stabilization at low power are substantially eliminated or reduced through a combination of chopping at low impedance nodes within the mixer amplifier and feedback. The signal path of the ADC operates as a continuous time system, providing minimal aliasing of noise or external signals entering the signal pathway at the chop frequency or its harmonics. In this manner, the chopper-stabilized ADC can be used in a low power system, such as an implantable medical device (IMD), to provide a stable, low-noise output signal.

45 Claims, 10 Drawing Sheets

U.S. PATENT DOCUMENTS

| | | | |
|---|---|---|---|
| 5,208,597 | A | 5/1993 | Early et al. |
| 5,311,876 | A | 5/1994 | Olsen et al. |
| 5,329,281 | A | 7/1994 | Baumgartner et al. |
| 5,369,309 | A | 11/1994 | Bacrania et al. |
| 5,392,042 | A | 2/1995 | Pellon |
| 5,477,481 | A | 12/1995 | Kerth |
| 5,606,320 | A | 2/1997 | Kleks |
| 5,647,379 | A | 7/1997 | Meltzer |
| 5,663,680 | A | 9/1997 | Nordeng |
| 5,697,958 | A | 12/1997 | Paul et al. |
| 5,742,246 | A | 4/1998 | Kuo et al. |
| 5,766,227 | A | 6/1998 | Nappholz et al. |
| 5,928,272 | A | 7/1999 | Adkins et al. |
| 6,061,593 | A | 5/2000 | Fischell et al. |
| 6,064,257 | A | 5/2000 | Sauer |
| 6,064,326 | A | 5/2000 | Krone et al. |
| 6,100,834 | A | 8/2000 | Lewyn |
| 6,130,578 | A | 10/2000 | Tang |
| 6,184,811 | B1 | 2/2001 | Nagari et al. |
| 6,262,626 | B1 | 7/2001 | Bakker et al. |
| 6,354,299 | B1 | 3/2002 | Fischell et al. |
| 6,360,123 | B1 | 3/2002 | Kimchi et al. |
| 6,362,763 | B1 | 3/2002 | Wang |
| 6,389,315 | B1 | 5/2002 | Schu et al. |
| 6,456,159 | B1 | 9/2002 | Brewer |
| 6,535,153 | B1 | 3/2003 | Zierhofer |
| 6,556,859 | B1 | 4/2003 | Wohlgemuth et al. |
| 6,567,025 | B2 | 5/2003 | Schreier et al. |
| 6,584,157 | B1* | 6/2003 | Van Der Zwan et al. .... 341/143 |
| 6,584,351 | B1 | 6/2003 | Ekwall |
| 6,625,436 | B1 | 9/2003 | Tolson et al. |
| 6,700,520 | B1 | 3/2004 | Miller |
| 6,707,409 | B1 | 3/2004 | Ignjatovic et al. |
| 6,760,623 | B2 | 7/2004 | Stahmann et al. |
| 6,810,285 | B2 | 10/2004 | Pless et al. |
| 6,924,760 | B1 | 8/2005 | McLeod et al. |
| 6,999,014 | B2 | 2/2006 | Oliaei et al. |
| 7,006,872 | B2 | 2/2006 | Gielen et al. |
| 7,015,853 | B1 | 3/2006 | Wolff et al. |
| 7,049,990 | B2 | 5/2006 | Ranganathan |
| 7,053,807 | B1 | 5/2006 | Gaalaas |
| 7,061,416 | B2 | 6/2006 | Nagai |
| 7,079,061 | B2 | 7/2006 | Schuurmans |
| 7,098,823 | B2 | 8/2006 | O'Dowd et al. |
| 7,098,827 | B2* | 8/2006 | Motz .......................... 341/143 |
| 7,102,558 | B2 | 9/2006 | Deval |
| 7,129,875 | B1 | 10/2006 | Altun et al. |
| 7,142,142 | B2 | 11/2006 | Petersen et al. |
| 7,142,143 | B2 | 11/2006 | Draxelmayr |
| 7,146,218 | B2 | 12/2006 | Esteller et al. |
| 7,176,817 | B2 | 2/2007 | Jensen |
| 7,215,269 | B2 | 5/2007 | Lee et al. |
| 7,221,303 | B1 | 5/2007 | Melanson |
| 7,230,555 | B2 | 6/2007 | Dolazza et al. |
| 7,233,198 | B2 | 6/2007 | Niederkorn |
| 7,245,246 | B2 | 7/2007 | Ihs et al. |
| 7,304,592 | B2 | 12/2007 | Pinna et al. |
| 7,345,607 | B1 | 3/2008 | Frigaard et al. |
| 7,355,539 | B2 | 4/2008 | Petersen et al. |
| 7,358,880 | B1* | 4/2008 | Melanson ................. 341/143 |
| 7,362,255 | B1* | 4/2008 | Tsyrganovich ............. 341/172 |
| 7,375,666 | B2 | 5/2008 | Melanson |
| 7,414,557 | B2 | 8/2008 | Andersson et al. |
| 2003/0146786 | A1 | 8/2003 | Gulati et al. |
| 2003/0184464 | A1 | 10/2003 | Nakamura et al. |
| 2004/0141558 | A1 | 7/2004 | Plisch et al. |
| 2005/0081847 | A1 | 4/2005 | Lee et al. |
| 2005/0128111 | A1 | 6/2005 | Brooks |
| 2005/0162222 | A1 | 7/2005 | Hezar et al. |
| 2006/0055456 | A1 | 3/2006 | Niederkorn |
| 2006/0135877 | A1 | 6/2006 | Giftakis et al. |
| 2006/0139192 | A1 | 6/2006 | Morrow et al. |
| 2006/0139193 | A1 | 6/2006 | Morrow et al. |
| 2006/0164272 | A1 | 7/2006 | Philips et al. |
| 2006/0173501 | A1 | 8/2006 | Stickney et al. |
| 2006/0250291 | A1 | 11/2006 | Lyden et al. |
| 2006/0293720 | A1 | 12/2006 | DiLorenzo |
| 2007/0032734 | A1 | 2/2007 | Najafi et al. |
| 2007/0077907 | A1 | 4/2007 | Rector |
| 2007/0152865 | A1 | 7/2007 | Melanson |
| 2007/0208262 | A1 | 9/2007 | Kovacs |
| 2007/0216562 | A1* | 9/2007 | Teo et al. ..................... 341/155 |
| 2009/0079607 | A1 | 3/2009 | Denison et al. |

FOREIGN PATENT DOCUMENTS

| | | |
|---|---|---|
| EP | 1 777 825 A1 | 4/2007 |
| GB | 1 249 395 | 10/1971 |
| WO | WO 99/12264 | 3/1999 |
| WO | WO 02/01711 | 1/2002 |
| WO | WO 02/03087 | 1/2002 |
| WO | WO 2006/066098 | 6/2006 |

OTHER PUBLICATIONS

Yen et al., "Micro-power low-offset instrumentation amplifier IC design for biomedical system applications," IEEE Transactions on Circuits and Systems, vol. 51, No. 4, pp. 691-699, Apr. 2004.

Harb et al., "New CMOS instrumentation amplifier dedicated to very low-amplitudesignal applications," Proceedings of ICECS, vol. 1, pp. 517-520, Sep. 1999.

Gosselin et al., "An ultra low-power chopper stabilized front-end for multichannel corrtical signals recording," Electrical and Computer Engineering, vol. 4, pp. 2259-2262, May 2004.

Harrison et al., "Local Field Potential Measurement with Low-Power Analog Integrated Circuit," Engineering in Medicine and Biology Society, 2004, IEMBS '04, $26^{th}$ Annual International Conference of the IEEE, vol. 2, On pp. 4067-4070 vol. 6, Sep. 1-5, 2004.

Martins et al., "A CMOS IC for Portable EEG Acquisition Systems," IEEE Transactions on Instrumentation and Measurement, vol. 47, No. 5, pp. 1191-1196, Oct. 1998.

Boser, "Capacitive Interfaces for Monolithic Integrated Sensors," Chapter in "RF Analog-to-Digital Converters; Sensor and Actuator Interfaces; Low-Noise Oscillators, PLLs and Synthesizers," R.J. van de Plaasche, J.H. Huijsing, and W.M.C. Sansen (eds.), Kluwer Academic Publishers, Nov. 1997, 20 pages.

Bakker et al., "A CMOS Nested-Chopper Instrumentation Amplifier with 100-nV Offset," IEEE Journal of Solid-State Circuits, vol. 35, No. 12, pp. 1877-1883, Dec. 2000.

Sanduleanu et al., "A Low Noise, Low Residual Offset, Chopped Amplifier for Mixed Level Applications," IEEE, 0-7803-5008-1/98, pp. 333-336, Sep. 1998.

Hadiashar et al., "A Chopper Stabilized CMOS Analog Multiplier with Ultra Low DC Offsets," Solid-State Circuits Conference, pp. 364-367, Sep. 2006.

Yiqian Ying, "Chopper Stabilized Amplifiers," Term Paper, Department of Electrical and Computer Engineering, University of Tortonto, 17 pgs., Nov. 12, 2001.

Yazicioglu et al., "60uW 60nV/rtHz Readout Front-End for Portable Biopotential Acquisition Systems," ISSCC Digest of Technical Papers 2006, paper 2.6, Feb. 2006, 2 pages.

Makinwa, "Dynamic Offset Cancellation Techniques," Smart Sensor Systems '02, May 2002, 42 pgs.

Ng et al., "A CMOS Analog Front-End IC for Portable EEG/ECG Monitoring Applications," IEEE Trans. On Circuits and Systems, vol. 52, No. 11, Nov. 2005, 13 pgs.

Burt et al., "A Micropower Chopper-Stabilized Operational Amplifier using an SC Notch Filter with Synchronous Integration inside the Continuous-Time Signal Path," ISSCC Digest of Technical Papers 2006, paper 19.6, Feb. 2006, 2 pgs.

Harrison et al., "Low-Power Low-Noise CMOS Amplifier for Neural Recording Applications," IEEE J. of Solid-State Circuits, vol. 38, No. 6, pp. 958-965, Jun. 2003, 8 pgs.

Wu et al., "A 1V 2.3mW Biomedical Signal Acquisition IC," ISSCC Digest of Technical Papers 2006, paper 2.7, Feb. 2006, 2 pgs.

Harrison et al., "A Low-Power Integrated Circuit for a Wireless 100-Electrode Neural Recording System," ISSCC Digest of Technical Papers 2006, paper 30.2, Feb. 2006.

U.S. Appl. No. 11/861,920, filed Sep. 26, 2007 entitled Implantable Medical Device with Low Power Delta-Sigma Analog-to-Digital Converter, by Terry et al.

U.S. Appl. No. 11/861,945, filed Sep. 26, 2007 entitled Detecting Overloading of an Analog-to-Digital Converter of an Implantable Medical Device, by Heinks et al.

U.S. Appl. No. 11/861,856, filed Sep. 26, 2007 entitled Method of EMI Detection for an Implantable Medical Device Sensor Channel That Uses a Delta-Sigma Type ADC by Monitoring the DAC Modulation Characteristics, by Heinks et al.

Declaration Under 37 C.F.R. 1.132, 3 pgs., (signed by Michael W. Heinks on Apr. 20, 2009).

Peter G. Blanken et al., "A 10μV-Offset 8kHz Bandwidth $4^{th}$-Order Chopped Sigma-Delta A/D Converter for Battery Management," Solid-State Circuits Conference, 2002, Digest of Technical Papers, 2002 IEEE International Feb. 3-7, 2002, vol. 1, Feb. 3, 2002, pp. 388-476 (XP-010585620).

International Search Report and Written Opinion from corresponding PCT Application Serial No. PCT/US2008/073458 mailed Feb. 3, 2009 (12 pages).

Reply to Written Opinion for corresponding corresponding PCT Application Serial No. PCT/US2008/073458, filed Jul. 23, 2009, 19 pages.

U.S. Appl. No. 11/609,388, filed Dec. 12, 2006, entitled "Method and Apparatus br Detection of Nervous System Disorders," by Carlson et al.

U.S. Appl. No. 11/700,404, filed Jan. 31, 2007, entitled "Chopper-Stabilized Instrumentation Amplifier for Wireless Telemetry," by Denison.

U.S. Appl. No. 11/700,405, filed Jan. 31, 2007, entitled "Chopper-Stabilized Instrumentation Amplifier for Impedance Measurement," by Denison et al.

Notification of Transmittal of the International Preliminary Report on Patentability for corresponding PCT Application Serial No. PCT/US2008/073458, dated Oct. 29, 2009 (14 pgs.).

* cited by examiner

CHOPPER-STABILIZED ANALOG-TO-DIGITAL CONVERTER

TECHNICAL FIELD

This disclosure relates to analog-to-digital converters (ADCs) and, more particularly, ADCs for low noise applications.

BACKGROUND

Sigma delta analog-to-digital converters (ADCs) are used in circuits to accurately convert a variety of test and measurement signals to digital values. Often, sigma delta ADCs are used in very low frequency applications that require high resolution. For example, a sigma delta ADC may be incorporated in a biopotential sensing circuit, i.e., a circuit configured to measure physiological signals, such as electrocardiogram (ECG), electromyogram (EMG), electroencephalogram (EEG), pressure, tissue impedance, and motion signals.

Measuring intrinsic and evoked biopotentials requires amplifying authentic signals on the order of microvolts while rejecting large polarization potentials and environmental noise on the order of volts. In addition to these external disturbances, sigma delta ADCs fabricated with sub-micron processes have the additional burden of rejecting random telegraph signal (RTS) noise, also referred to as popcorn noise. RTS noise can produce random offsets that, some applications, may be large enough to be erroneously classified as sense events. Hence, RTS noise in an ADC can undermine the accuracy of a sensing device.

SUMMARY

This disclosure describes a chopper-stabilized sigma-delta analog-to-digital converter (ADC). The ADC may be configured to provide accurate output at low frequency with very low power. The ADC incorporates a mixer amplifier to substantially reduce or eliminate noise and offset from an output signal produced by the mixer amplifier. Dynamic limitations, i.e., glitching that result from chopper stabilization at low power are substantially eliminated or reduced through a combination of chopping at low impedance nodes within the mixer amplifier and feedback. The signal path of the ADC operates as a continuous time system, and may provide minimal aliasing of noise or external signals entering the signal pathway at the chop frequency or its harmonics. In this manner, the chopper-stabilized ADC can be used in a low power system, such as an implantable medical device (IMD), to provide a stable, low-noise output signal.

In one embodiment, the disclosure provides a chopper-stabilized analog-to-digital converter (ADC) comprising a first modulator and a mixer amplifier. The first modulator modulates an amplitude of an analog input signal at a clock frequency to produce a modulated signal. The mixer amplifier amplifies the modulated signal to produce an amplified signal and demodulates the amplified signal at the clock frequency to produce an output signal. The ADC further comprises circuitry that converts the output signal into a digital value that approximates the analog input signal, circuitry that converts the digital value into reconstructed analog output signal, a second modulator that modulates an amplitude of the reconstructed analog output signal at the clock frequency, and a feedback path that applies the modulated output signal as a feedback signal to the modulated input signal.

In another embodiment, the disclosure provides a physiological sensing device comprising a physiological sensor that generates an input signal indicative of a physiological condition, and a chopper-stabilized analog-to-digital converter (ADC). The chopper-stabilized ADC further comprises a first modulator that modulates an amplitude of the input signal at a clock frequency to produce a modulated signal, a mixer amplifier that amplifies the modulated signal to produce an amplified signal and demodulates the amplified signal at the clock frequency to produce an output signal, circuitry that converts the output signal into a digital value that approximates the analog input signal, circuitry that converts the digital value into reconstructed analog output signal, a second modulator that modulates an amplitude of the reconstructed analog output signal at the clock frequency, and a feedback path that applies the modulated output signal as a feedback signal to the modulated input signal.

In an additional embodiment, the disclosure provides a chopper-stabilized analog-to-digital (ADC) converter comprising means for modulating an amplitude of an analog input signal at a clock frequency to produce a modulated signal, means for amplifying the modulated signal to produce an amplified signal and demodulating the amplified signal at the clock frequency to produce an output signal, means for converting the output signal into a digital value that approximates the analog input signal, means for converting the digital value into a reconstructed analog output signal, means for modulating an amplitude of the reconstructed analog output signal at the clock frequency, and means for applying the modulated output signal as a feedback signal to the modulated input signal.

In a further embodiment, the disclosure provides a method comprising modulating an amplitude of an analog input signal at a clock frequency to produce a modulated signal, amplifying the modulated signal in a mixer amplifier to produce an amplified signal, demodulating the amplified signal in the mixer amplifier at the clock frequency to produce an output signal, converting the output signal into a digital value that approximates the analog input signal, converting the digital value into a reconstructed analog output signal, modulating an amplitude of the reconstructed analog output signal at the clock frequency, and applying the modulated output signal as a feedback signal to the modulated input signal via a first feedback path.

The details of one or more example embodiments are set forth in the accompanying drawings and the description below. Other features, objects, and advantages of the techniques will be apparent from the description and drawings, and from the claims.

DETAILED DESCRIPTION

Figure 1:
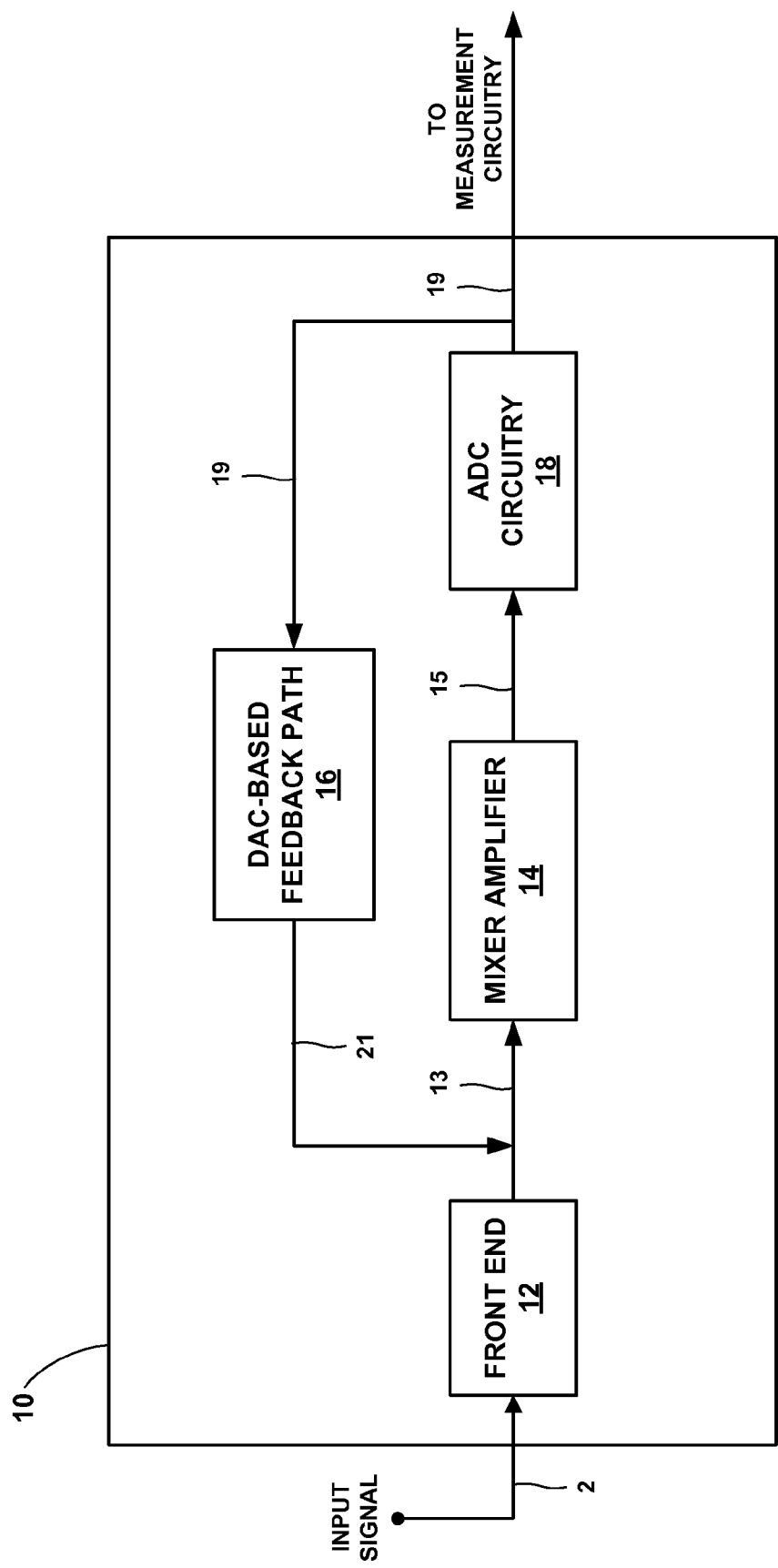
FIG. 1 is a block diagram illustrating a chopper stabilized analog-to-digital converter (ADC) that incorporates a mixer amplifier.

This disclosure describes a chopper-stabilized sigma-delta analog-to-digital converter (ADC). The ADC may be configured to provide accurate output at low frequency with relatively low power. The ADC includes a mixer amplifier to substantially eliminate noise and offset from an output signal produced by the mixer amplifier. Dynamic limitations, i.e., glitching that result from chopper stabilization at low power are substantially eliminated or reduced through a combination of chopping at low impedance nodes within the mixer amplifier and feedback. The signal path of the ADC operates as a continuous time system, which may provide minimal aliasing of noise or external signals entering the signal pathway at the chop frequency or its harmonics. In this manner, the chopper-stabilized ADC can be used in a low power system, such as an implantable medical device (IMD), to provide a stable, low-noise output signal.

The chopper-stabilized ADC may be incorporated in a biopotential sensing circuit, i.e., a circuit configured to measure physiological signals, such as electrocardiogram (ECG), electromyogram (EMG), electroencephalogram (EEG), pressure, impedance, motion signals, and other signals. However, the ADC may be useful not only in biomedical measurement applications, but also in general purpose test and measurement applications and, more particularly, general purpose test and measurement applications that operate at low frequency with relatively low power.

In general, a chopper-stabilized ADC, as described in this disclosure, may be configured for low power applications. An IMD, for example, may be characterized by finite power resources that are required to last several months or years. Accordingly, to promote device longevity, sensing and therapy circuits are generally designed to consume relatively small levels of power. As an example, operation of a sensor circuit incorporating an ADC, as described in this disclosure, may require a supply current of less than 2.0 microamps, and more preferably less than 1.0 microamps. In some embodiments, such a sensor circuit may consume supply current in a range of approximately 100 nanoamps to 1.0 microamps. Such a sensing circuit may generally be referred to as a micropower sensing circuit. Although medical devices are described for purposes of illustration, a micropower sensing circuit may be used in a variety of medical and non-medical test and measurement applications. In each case, the micropower sensing circuit may be required to draw low power, yet provide precise and accurate measurement.

According to various embodiments of this disclosure, a chopper-stabilized ADC may include a front end, a first chopper, an amplifier, a second chopper, an integrator in the form of a baseband amplifier with high gain and compensation, analog-to-digital converter (ADC) circuitry, and a feedback path that includes a digital-to-analog converter (DAC). The amplifier, second chopper, and integrator may be referred to collectively as a mixer amplifier. The signal path of the ADC operates as a continuous time system, reducing aliasing of noise or other undesirable signals entering the signal pathway at the chop frequency or its harmonics. The front end generates an input signal in the baseband, i.e., the frequency band of interest for purposes of the test or measurement application. The baseband also may be referred to as the measurement band. The feedback path provides negative feedback that minimizes the error between the low frequency analog input signal and the output of the ADC circuitry.

Amplification of the input signal can introduce DC offset and low frequency noise, such as random telegraph signal (RTS) noise, 1/f noise, and offset due to amplifier imperfection or other factors. RTS noise is also referred to as popcorn noise. To reduce DC offset and low frequency noise, a first chopper stage in the front end modulates the input signal at a chopper frequency prior to application of the input signal to the mixer amplifier. After the input signal is amplified, the second chopper within the mixer amplifier demodulates the input signal at the chopper frequency to produce an amplified output signal in the baseband. This process confines the noise and offset generated by the amplifier to the chopper frequency band, thereby preventing it from entering the measurement band. As a result, the output of the mixer amplifier is a stable, low noise signal.

The ADC circuitry generates a digital bit stream value based on the output of the mixer amplifier. The DAC produces a reconstructed representation of the analog input signal using the digital value and applies the reconstructed representation to the input signal. In this way, the output of the DAC is applied to the analog input signal to keep the signal change at the input to the mixer amplifier small. As a result, the ADC can track changes in the low frequency analog input signal and output an accurate approximation of the input signal while operating at very low power.

The mixer amplifier may have a modified folded cascode amplifier architecture in which the signal is chopped at low impedance nodes to provide fast modulation dynamics. The mixer amplifier substantially removes the noise and offset at the chopper frequency from the demodulated signal, and thereby passes a low noise signal to the measurement band. When the mixer amplifier is operating at low power, however, the bandwidth of the amplifier can be limited. Limited bandwidth can result in glitching, i.e., ripple or spikes, in the output signal.

An ADC as described in this disclosure may provide a negative feedback to keep the signal change at the input to the mixer amplifier relatively small. The negative feedback loop may eliminate or reduce glitching resulting from the limited bandwidth of the mixer amplifier. As a result, the ADC is configured to achieve a stable, low noise output while drawing relatively low current from a power source.

Various example embodiments are presented. According to one example embodiment, which is useful when the ADC senses a difference in voltage across its inputs, the front end may include a continuous time switched capacitor network. In an ADC using a differential architecture, for example, the switched capacitor network includes a differential set of switched input capacitors that toggle between input voltages at a chop frequency. By chopping the switched input capacitors, the input differential signal is up-modulated to a chopper frequency, yielding a modulated signal at the differential input of the mixer amplifier. In another example embodiment, ADC may use a single-ended architecture instead of a differential architecture.

An ADC utilizing the chopper stabilization techniques described herein may be useful when incorporated as part of a biopotential sensing circuit for electroencephalography (EEG) and physiological signal monitoring applications such as posture and activity monitoring with accelerometers, catheter monitoring with pressure sensors, other pressure-related physiological monitoring, monitoring of heart sounds, monitoring of brain signals, and other physiological monitoring applications that would benefit from micro power systems for precision sensor measurements.

Physiological signals are generally found at low frequencies, e.g., less than or equal to approximately 100 Hz and, in many cases, less than or equal to approximately 2 Hz, or even less than or equal to approximately 1 Hz. Measurement and analysis of physiological signals can be used to diagnose chronic or acute disease states and other medical conditions. Example physiological signals include EEG signals, ECG signals, EMG signals, pressure, impedance, and motion signals, as previously described. Such signals may be used to detect or measure cardiac ischemia, pulmonary edema, breathing, activity, posture, pressure, brain activity, gastrointestinal activity, and the like.

IMDs including biopotential sensing circuits that incorporate an ADC are used to measure such physiological signals. However, measuring intrinsic and evoked biopotentials may require amplifying authentic signals on the order of microvolts while rejecting large polarization potentials and environmental noise on the order of volts. In addition to these external disturbances, RTS or popcorn noise, as well as 1/f noise and offset can enter the signal path. This can lead to oversensing phenomena that might result in withholding needed therapy or providing therapy when it is not needed. In particular, offset or other spurious signals may cause erroneous detection of sense events. Sense events may be used as the basis to deliver or withhold therapy such as cardiac stimulation, neurostimulation, drug dosage or the like. Accordingly, accurate detection is important in many therapeutic or diagnostic applications.

In addition, biopotential sensing circuits may be required to operate with low noise and low power. Low power consumption may be especially important in IMDs designed for several years of services, and particularly those medical devices configured to sense physiological signals and deliver therapies. Examples of therapeutic medical devices designed fro chronic implantation are implantable cardiac pacemakers, implantable cardioverter-defibrillators, implantable electrical stimulators, such as neurostimulators, muscle stimulators or other tissue stimulators, implantable drug delivery devices, and other devices.

It is important that an ADC in a biopotential sensing circuit provide low noise performance so that noise does not result in reduced sensitivity or wrong or misleading diagnostic information. It is also important that the ADC operate with low power in order to conserve limited battery resources and thereby promote operational longevity of the implantable medical device. A chopper-stabilized ADC, as described in various embodiments of this disclosure, may be configured to provide an accurate output at low frequency with low power. As will be described, a chopper-stabilized ADC can be configured to apply chopping at low impedance nodes and apply feedback to reduce ripple resulting from low bandwidth of the amplifier.

FIG. 1 is a block diagram illustrating a chopper-stabilized ADC 10 that is configured to provide stable, i.e., low noise, output at low frequency with relatively low power. ADC 10 uses chopping at the inputs to a mixer amplifier 14 to substantially reduce or eliminate random telegraph signal (RTS) noise, 1/f noise, and offset from an output produced by the amplifier (output 15 in FIG. 1). RTS noise is also referred to as popcorn noise. Dynamic limitations, i.e., glitching, that result from chopper stabilization at low power may be substantially reduced or eliminated through a combination of chopping at low impedance nodes within mixer amplifier 14 and feedback via a digital-to-analog converter (DAC)-based feedback path 16.

The signal path of ADC 10 operates as an oversampled data system, providing minimal aliasing of noise or external signals entering the signal pathway at the chop frequency or its harmonics. As a result, ADC 10 can provide a low noise output that accurately represents low frequency continuous time analog input signals while operating under the constraints of a micro power system, e.g., drawing a supply current of less than or equal to approximately 2.0 microamps, and more preferably less than or equal to approximately 1.0 microamps, and requiring a supply voltage of less than or equal to approximately 2.0 volts, and more preferably less than or equal to approximately 1.5 volts. Example low frequency signals include physiological signals and other signals having a frequency of less than approximately 100 Hz, and preferably less than or equal to approximately 2.0 Hz, and more preferably less than or equal to approximately 1.0 Hz.

As shown in FIG. 1, ADC 10 includes front end 12, mixer amplifier 14, analog-to-digital converter (ADC) circuitry 18, and DAC-based feedback path 16. In general, ADC 10 is configured to convert low frequency analog input signal 2 into a digital signal 19. Analog input signal 2 may be obtained from any of a variety of sensors, such as an accelerometer, an electrode sensor interface, a pressure sensor, or the like. DAC-based feedback path 16 converts digital signal 19 into a reconstructed representation 21 of input signal 2, and forms a negative feedback path that applies signal 21 as a feedback signal to input signal 2 to produce signal 13. Because signal 21 is a reconstructed representation of analog input signal 2, signal 13 represents the difference between analog input signal 2 and reconstructed signal 21. Typically, signal 13 is small because analog input signal 2 does not experience large signal changes. Consequently, ADC 10 can track changes in analog input signal 2 to produce digital signal 19 as an accurate approximation of input signal 2.

In the example of FIG. 1, front end 12 may provide a switched or static capacitive interface to mixer amplifier 14, e.g., for measurement of a low frequency voltage amplitude of input signal 2. Front end 12 chops analog input signal 2 to produce a modulated (chopped) input signal that carries a low frequency signal of interest on a carrier (chopper) frequency and couples the signal to mixer amplifier 14. In one embodiment, front end 12 may operate using a differential architecture to produce a differential modulated input signal. Alternatively, front end 12 may produce a single-ended modulated input signal. In FIG. 1, front end 12 couples modulated signal 13 to the inputs of mixer amplifier 14. As will be described in detail, the output of front end 12 is combined with the output of DAC-based feedback path 16, i.e., signal 21, to produce modulated signal 13. In this way, front end 12 shifts a low frequency signal that is subject to introduction of low frequency noise by mixer amplifier 14 to a carrier frequency at which the mixer amplifier 14 does not introduce substantial noise into the signal.

The low frequency signal of interest may have, for example, a frequency within a range of 0 to approximately 100 Hz, preferably less than or equal to approximately 2.0 Hz, and more preferably less than or equal to approximately 1.0 Hz. In some embodiments, the carrier (chopper) frequency may be within a frequency range of approximately 4 kHz to 200 kHz. Front end 12 modulates the low frequency signal prior to introduction to mixer amplifier 14 so that the original baseband (low frequency) signal components are not corrupted by noise components introduced by mixer amplifier 14 at low frequency.

Noise generally enters the signal path of ADC 10 through mixer amplifier 14. However, mixer amplifier 14 should not introduce noise to the modulated signal at the carrier frequency. Rather, the noise components are typically present at low frequency and may include popcorn (RTS) noise and 1/f (flicker) noise. In addition, noise in the form of DC offset cannot be introduced at the carrier frequency. Mixer amplifier 14 amplifies the up-modulated input signal, i.e., signal 13, which is a combination of the low frequency analog input signal from front-end 12 and feedback signal 21. Again, signal 13 is up-modulated to the chopper (carrier) frequency to protect the signal of interest from noise and offset that occurs in the low frequency range.

Mixer amplifier 14 demodulates the modulated and amplified input signal from the carrier frequency to the baseband of interest while upmodulating the mixer amp 1/f noise and offset out of the measurement band. Thus, the original low frequency signal components are demodulated back to baseband, while the low frequency noise and offset components of the mixer amplifier 14 are modulated up to the higher frequency band, e.g, 4 kHz to 200 kHz. Mixer amplifier 14 passes only the baseband signals, i.e., signals with frequency components of approximately 100 Hz or less, as output and substantially reduces or eliminates the noise components located at the carrier frequency. Thus, the output of mixer amplifier, i.e., signal 15, contains the low frequency signal components of interest, but reduces or eliminates the low frequency noise and offset. In addition, mixer amplifier 14 provides a gain amplifier that amplifies modulated input signal 13. In this way, mixer amplifier 14 generates analog signal 15 as a low noise output while operating at low power.

ADC 10 and, more particularly, mixer amplifier 14 operates under the constraints of a micro power system and therefore has limited bandwidth. The limited bandwidth of mixer amplifier 14 can cause glitching or ripple in the passband of output signal 15. As will be described, mixer amplifier 14 may have a modified folded cascode architecture that provides switching, e.g., via CMOS switches, at low impedance nodes. Switching at low impedance nodes enables chopping at higher frequencies where the only limitation would be the charge injection residual offset.

DAC-based feedback path 16 is coupled between the output of mixer amp 14 and front end 12 to reduce ripple or glitching. Feedback path 16 substantially eliminates glitching in output signal 15 by driving the net input signal to mixer amplifier 14 toward zero. This can be achieved because DAC-based feedback path 16 generates signal 21 as a reconstructed representation of analog input signal 2 using the output of ADC circuitry 18. When signal 21 is a good (accurate) approximation, the difference or error between signal 21 and signal 2 is small. In this way, feedback path 16 keeps the signal change at the input of mixer amplifier 14 relatively small in steady state. As a result, mixer amplifier 14 outputs signal 15 as a stable, low noise signal while operating at low power.

ADC circuitry 18 processes low noise signal 15 to generate digital signal 19. The accuracy with which digital signal 19 represents analog input signal 2 is dependent on the quality of signal 15, i.e., the amount of noise in signal 15. Since noise, offset, and glitching are substantially eliminated or at least significantly reduced, digital signal 19 exhibits an increased accuracy in approximating analog input signal. Consequently, digital signal 19 provides a more accurate representation of low frequency analog input signal 2, and may thereby reduce oversensing that could result in withholding needed therapy or providing therapy when it is not needed.

ADC 10 may be useful in many different applications. This disclosure presents various example embodiments of ADC 10. However, these example embodiments should not be considered limiting of the ADC 10 as broadly embodied and described in this disclosure. Rather, it should be understood that the example embodiments described in this disclosure are a subset of many different example embodiments within the scope of this disclosure.

In some embodiments, a device such as an IMD may include multiple ADCs 10. For example, multiple ADCs 10 may be used to provide multiple sensing channels. The multiple sensing channels may sense the same type of physiological information, e.g., at different positions or angles, or via different sensors. In addition, multiple sensing channels may sense different types of physiological information, such as impedance, ECG, EEG, EMG, pressure, motion, and the like.

According to one example embodiment, front end 12 of ADC 10 may comprise a continuous time switched capacitor network that uses a differential configuration. The switched capacitor network includes a differential set of switched input capacitors that toggle between input voltages at the positive and negative terminals of ADC 10 and a differential set of switched input capacitors that modulate the output of DAC-based feedback path 16, i.e., signal 21. By toggling the switched input capacitors at the chopper frequency, input signal 2 and signal 21 are chopped. In this manner, these signals are up-modulated to the carrier frequency and combined, yielding modulated signal 13 at the differential input of mixer amplifier 14. In other example embodiments, however, front end 12 of ADC 10 may use a single-ended configuration instead of a differential configuration. In this example, ADC 10 may be implemented in a biopotential sensing circuit for measuring physiological voltage signals such as ECG, EEG, EMG, pressure, motion, posture, or the like. Accordingly, the inputs to front end 12 may be electrodes, or outputs from any of a variety of accelerometers, pressure sensors, strain gauge sensors, or the like.

ADC 10 can provide one or more advantages in a variety of embodiments. For example, as previously described, ADC 10 can provide accurate output at low frequency with low power. This is a result of the basic architecture of ADC 10. As another advantage, in example embodiments that implement feedback capacitors, on-chip, poly-poly capacitors may be used to implement the feedback capacitors in ADC 10. Poly-poly capacitors enable fast switching dynamics and can be formed on-chip with other amplifier components. A poly-poly capacitor may be formed on chip with other devices by combining two polysilicon electrodes and an intervening silicon dioxide dielectric. The gain of the ADC can be set by the ratio of the feedback capacitors to the input capacitors and centered around a selected reference voltage. In other example embodiments, the DAC of the negative feedback path may control the feedback ratio internally without the use of feedback capacitors. These advantages are merely exemplary and should be considered a subset of potential advantages provided by ADC 10. Additional advantages are discussed in this disclosure or may occur to those skilled in the art upon consideration of this disclosure. Moreover, such advantages may not coexist in every embodiment.

Figure 2A:
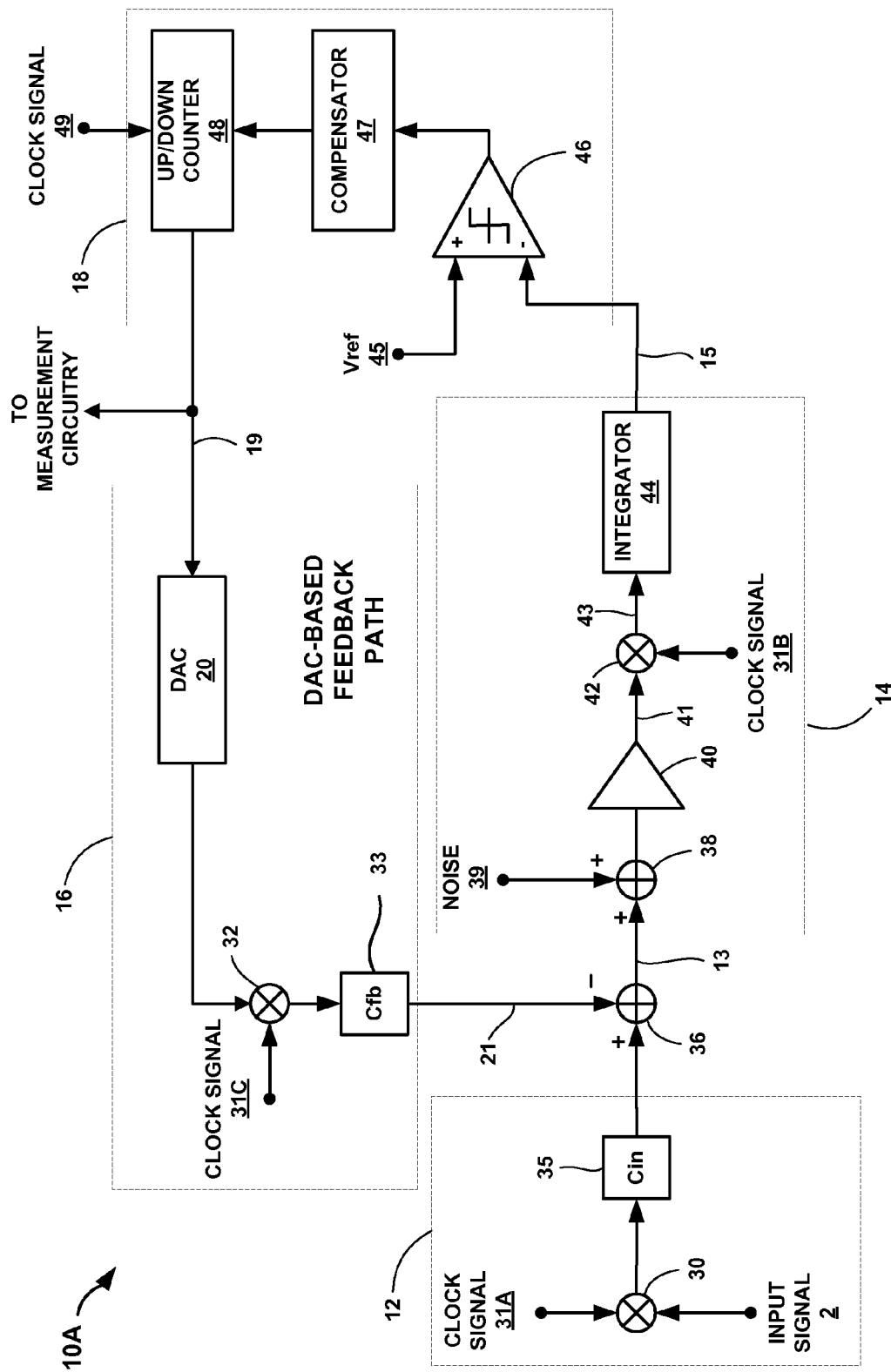
FIG. 2A is a diagram illustrating an example signal flow path of the chopper-stabilized ADC of FIG. 1.

FIG. 2A is a block diagram illustrating a signal path flow of an exemplary ADC 10A. Generally, the signal path flow in FIG. 2 begins with modulated signal 13 being applied to mixer amplifier 14. As previously described, mixer amplifier 14 produces signal 15 as a stable, low noise signal. ADC circuitry 18 converts low noise analog signal 15 into digital signal 19. Digital signal 19 may be a value whose average value approximates analog input signal 2. Feedback path 16 includes DAC 20 which converts digital signal 19 into analog signal 21 and applies analog signal 21 as negative feedback. This keeps the signal small at the input to mixer amplifier 14 thereby eliminating glitching in signal 15 that would otherwise be present because of the limited bandwidth of mixer amplifier 14. Consequently, ADC 10A produces digital signal 19 as an accurate approximation of low frequency input signal 2.

The following provides a more detailed description of the signal path flow depicted in FIG. 2A. In FIG. 2A, front end 12 includes modulator 30 for modulating a low frequency analog input signal 2 to produce a modulated signal that carries the baseband components of interest at a carrier frequency. An input capacitance (Cin) 35 couples the output of modulator 30 to summing node 36. As described above, front end 12 may use either a single-ended or differential configuration. For a differential signal, Cin 35 may include a first input capacitor coupled to a first input of a differential input mixer amplifier 14 and a second input capacitor coupled to a second input of mixer amplifier 14. For a single-ended signal, Cin 35 may include a single capacitor coupled to an input of single-ended input mixer amplifier 14.

Modulator 30 modulates an amplitude of input signal 2 at a carrier frequency provided by clock signal 31A. Clock signal 31A, like other clock signals described in this disclosure, may be a square wave signal that effectively multiples the signal by plus 1 and minus 1 at a desired clock frequency. In this manner, modulator 30 chops the input signal 2 up to the carrier (chop) frequency prior to application of the input signal to mixer amp 14. Modulator 30 may, in some embodiments that utilize a differential architecture, comprise a pair of complementary metal oxide semiconductor (CMOS) single pole, double throw (SPDT) switches that are driven by clock signal 21A to modulate (chop) input signal 32 to the carrier frequency. The CMOS SPDT switches may be cross-coupled to each other to reject common mode signals.

In one example embodiment, the CMOS switches may be coupled to a set of differential capacitors to form a continuous time switched capacitor network that forms input capacitance Cin at the input of mixer amplifier 14. In this case, front end 12 may be coupled to a physiological sensor that generates an input signal 2 proportional to a sensed physiological parameter at its outputs. For example, input signal 2 may be a differential output signal from a pair or electrodes, or from an accelerometer, pressure sensor, or the like.

Feedback summing node 36 will be described below in conjunction with feedback path 16. Summing node 38 represents the introduction of RTS (popcorn) noise, 1/f noise, and offset within mixer amplifier 14, noise 39 in FIG. 2A. Noise 39 may also include other external signals that may enter the signal pathway at a low (baseband) frequency. At summing node 38, the original low frequency components have been chopped to a higher (carrier) frequency by modulator 30. The original baseband signal components of input signal 13 may have a frequency within a range of 0 to approximately 100 Hz and the carrier frequency may be approximately 4 kHz to approximately 10 kHz. Thus, the low frequency noise 39 is segregated from the original low frequency components at the input to mixer amplifier 14.

Mixer amplifier 14 receives this noisy modulated input from node 38. In the example of FIG. 2, mixer amplifier 14 includes gain amplifier 40, modulator 42, and integrator 44. Amplifier 40 amplifies the noisy modulated input signal to produce amplified signal 41. Modulator 42 demodulates amplified signal 41 to produce demodulated signal 43. That is, modulator 42 modulates noise 39 up to the carrier frequency and demodulates the original baseband signal components from the carrier frequency back to baseband. Modulator 42 may comprise switches, e.g., CMOS SPDT switches, located at low impedance nodes within a folded-cascode architecture of mixer amplifier 14. Modulator 42 is supplied with clock signal 31B to demodulate amplified signal 41 at the same carrier frequency as clock signal 31A. Hence, clock signals 31A, 31B should be synchronous with each other. In some embodiments, clock signal 31A and clock signal 31B may be the same signal, i.e., supplied by the same clock.

Integrator 44 operates on demodulated signal 43 to pass the low frequency signal components at baseband and substantially eliminate noise components 39 which are located at the carrier frequency. In this manner, integrator 44 may be designed to provide a stable feedback path 16 with acceptable bandwidth while also filtering out the upmodulated RTS (popcorn) noise, 1/f noise, and offset from the measurement band. In other words, integrator 44 provides compensation and filtering. In other embodiments, compensation and filtering may be provided by other circuitry. However, the use of integrator 44 as described in this disclosure may be desirable. FIG. 3 provides a detailed circuit diagram of an example embodiment of mixer amplifier 14.

As will be described in detail, feedback path 16 provides negative feedback to the input of mixer amplifier 14 to reduce glitching in output signal 15. Because output signal 15 is a stable, low noise signal, ADC circuitry 18 generates digital signal 19 as a good (accurate) approximation of analog input signal 2. ADC circuitry 18 is illustrated in FIG. 2 as including comparator 46, compensator 47, and up/down counter 48. Generally, up/down counter 48 may be implemented as a multi-bit up/down counter. Accordingly, DAC 20 in feedback path 16 may also be implemented as a single or multi bit DAC that converts digital signal 19 output by ADC circuitry 18 into analog signal 21.

Comparator 46 controls up/down counter 48 by producing a signal that represents a binary 0 or 1 based on the comparison of signal 15 to a reference voltage, i.e., (Vref) 45 in FIG. 2. For example, when signal 15 exceeds Vref 45, comparator 46 outputs a signal that causes up/down counter 48 to count up. However, when Vref exceeds signal 15, comparator 46 outputs a signal that causes up/down counter 48 to count down. In some example embodiments, mixer amplifier 14 may generate a differential output that is provided to differential inputs of comparator 46. In this case, comparator is not coupled to Vref 45, but instead receives differential inputs from mixer amplifier 14. Instead, comparator 46 outputs a control signal that causes up/down counter 48 to count up when the differential signal of a positive input is greater than the differential signal of the negative input. Likewise, comparator 46 outputs a control signal that causes up/down counter 48 to count down when the differential signal of a positive input is less than the differential signal of the negative input.

ADC circuitry 18 generates digital signal 19 as a digital bit stream that approximates analog input signal 2. Compensator 47 stabilizes feedback path 16 by, for example, implementing a high pass filter, e.g., $1-1/2*(z-1)$, that assists in stabilizing feedback path 16. The combination of integrator 44 and up/down counter 48 operates as a double integrator. The high pass filter provided by compensator 47 provides stability.

Figure 4:
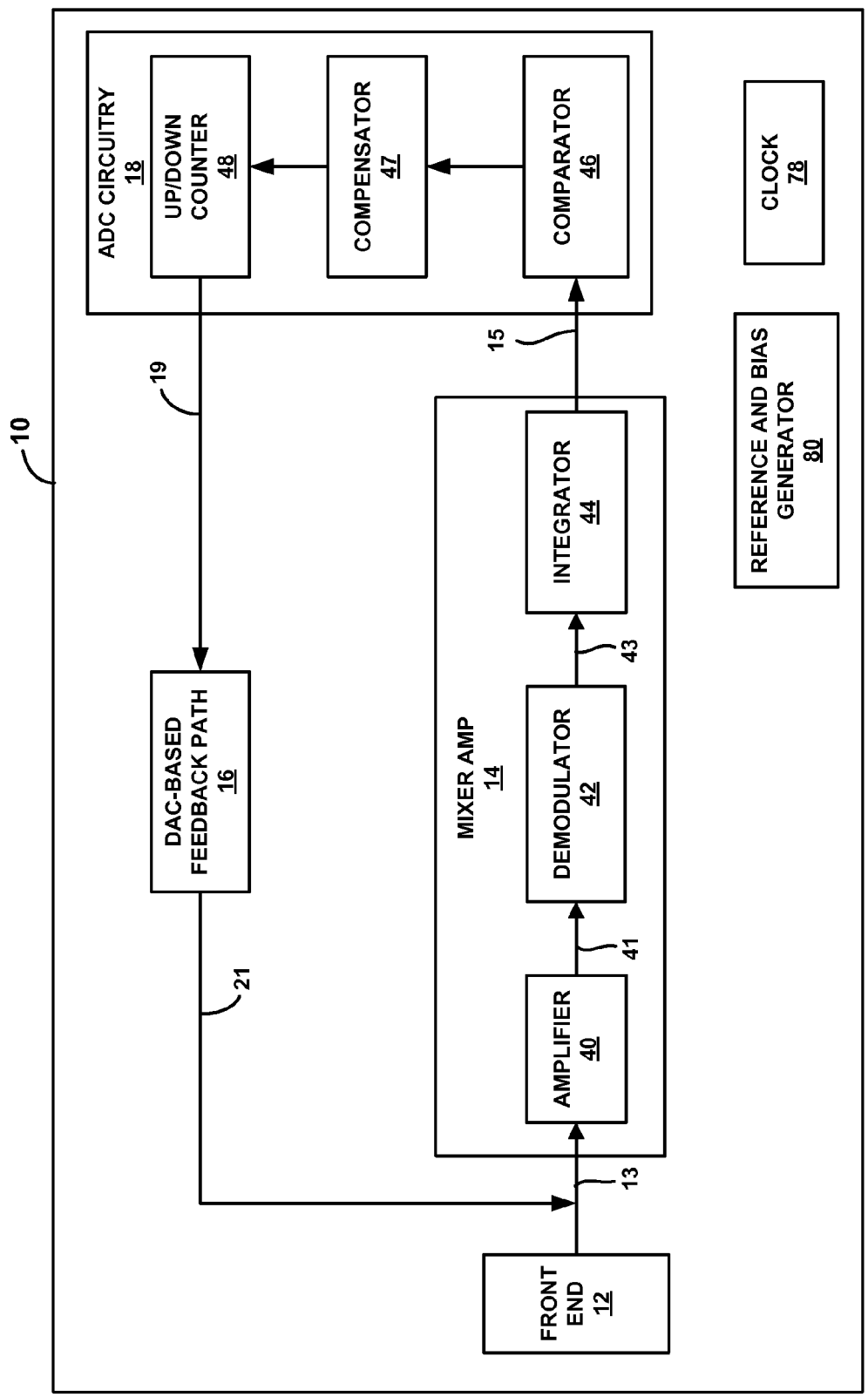
FIG. 4 is a block diagram illustrating an example embodiment of the chopper-stabilized ADC of FIG. 1 in greater detail.

Clock signal 49 drives up/down counter 48 to generate an output for every clock cycle. Clock signal 49 may be different than clock signals 31. In one example embodiment, for example, clock signal 31 may be operating at 16 kHz while clock signal 49 is operating at 16 or 32 kHz. The output of up/down counter 48 may be provided to measurement circuitry, e.g., via a decimation filter. The decimation filter may average the last 16 or 32 samples and output the digital result every 1 ms (1 kHz). In other words, the feedback loop of the ADC integrates the error between input signal 2 and reconstructed signal 21 at approximately 16 or 32 times the rate at which the digital signal is output by measurement circuitry. The digital output, i.e. signal 19, exhibits jitter, even when analog signal 15 is stable. Accordingly, analog-to-digital conversion may be provided by other circuit components or techniques. For example, more complex ADC circuitry may be used to eliminate the flicker or bit bobble caused by counting up or down every clock cycle. Other circuits may occur to those skilled in the art upon consideration of this disclosure. Thus, ADC circuitry 18 as shown in FIG. 4 should not be considered limiting of the invention as broadly described in this disclosure in any way.

DAC 20 may be a single or multi-bit DAC that uses digital signal 19 to generate signal 21 as a reconstructed representation of input signal 2 and forms feedback path 16 that applies signal 21 as negative feedback to the input of mixer amplifier 14 to reduce glitching in output signal 15. In particular, feedback path 16 drives the input to mixer amplifier 14, i.e. modulated signal 13, toward zero in steady state. This is achieved because modulated signal 13 is the combination of analog input signal 2 and an approximation of input signal 2 generated by DAC 20. Provided that analog input signal 2 does not exhibit a large signal change, modulated signal 13 is small because ADC 10A provides a good approximation of input signal 2, as described in this disclosure.

In FIG. 2A, feedback path 16 includes a modulator 32, which modulates signal 21 to produce a feedback signal that is added to the signal path between front end 12 and mixer amplifier 14 at node 36. In one example embodiment, the feedback signal generated by modulator 32 is a differential feedback signal. In other example embodiments, however, the feedback signal may be a single-ended signal. Feedback path 16 of FIG. 2A provides capacitor scaling versus input capacitance Cin 35 of mixer amplifier 14 to produce attenuation and thereby generate gain at the output of mixer amplifier 14. Accordingly, feedback path 16 may include a feedback capacitance (Cfb) 33 that is selected to produce desired gain, given the value of the input capacitance (Cin) 35 of mixer amplifier 14.

Clock signal 31C drives modulator 32 in feedback path 16 to modulate the output of DAC 20, i.e., signal 21, at the carrier frequency. Clock signal 31C may be derived from the same clock as clock signals 31A, 31B. In the case of differential feedback, feedback path 16 may include two feedback paths that apply the negative feedback to the positive and negative input terminals of mixer amplifier 14. Thus, the two feedback paths of feedback path 16 should be 180 degrees out of phase with each other, with one of the feedback paths modulating synchronously with modulators 30 and 42. This ensures that a negative feedback path exists during each half of the clock cycle.

As an alternative, in some embodiments, mixer amplifier 14 may be configured to generate a differential output signal, rather than a single-ended output signal. A differential output signal may provide positive and negative outputs. In this case, feedback path 16 can feed back the positive output to the positive input of mixer amplifier 14 and feed back the negative output to the negative input of the mixer amplifier. For a differential output signal, feedback path 16 would modulate each of the positive and negative outputs. However, the positive and negative outputs could be modulated in-phase, rather than out of phase.

Figure 2B:
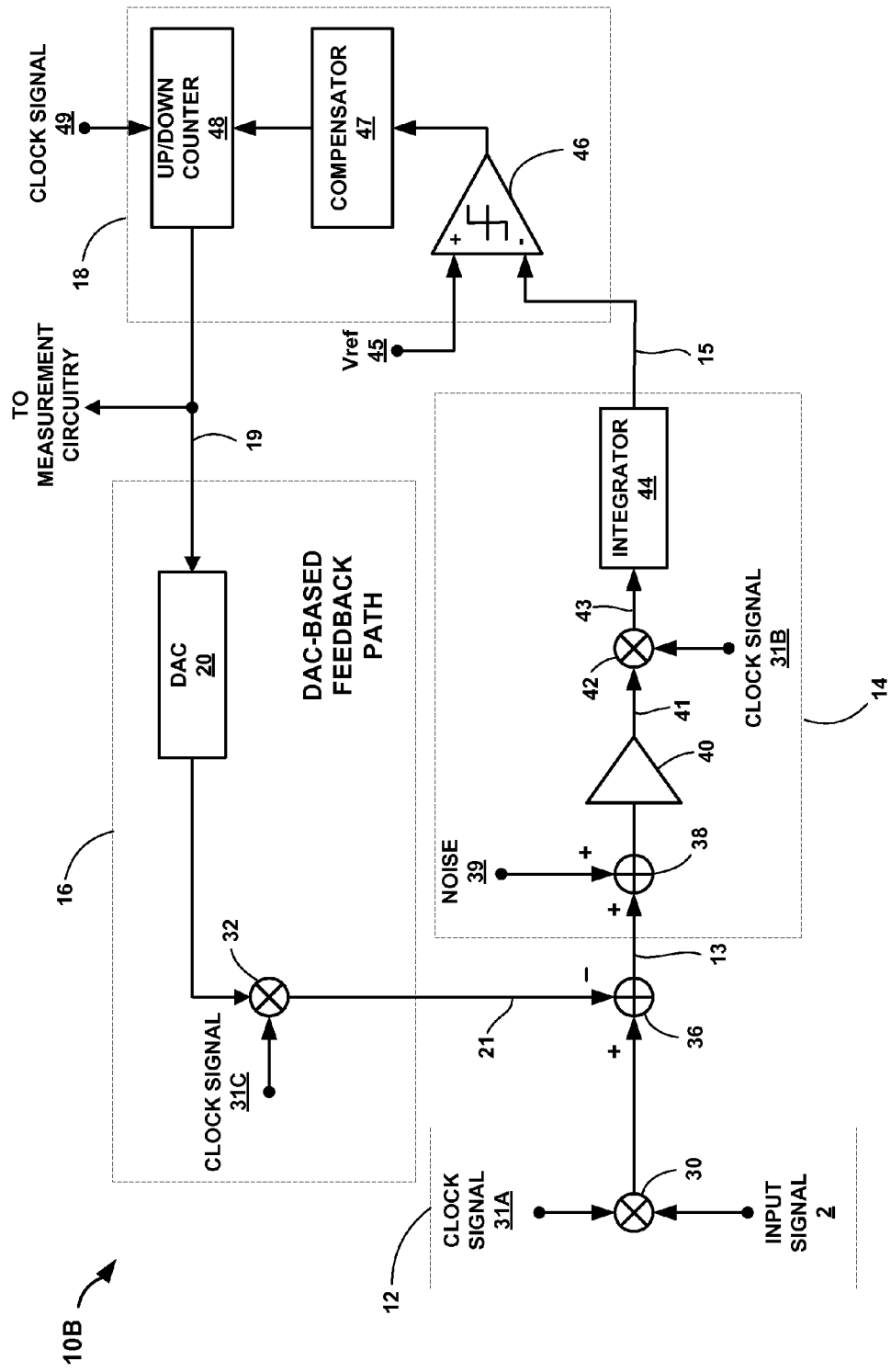
FIG. 2B is a diagram illustrating another example signal flow path of the chopper-stabilized ADC of FIG. 1.

FIG. 2B is a block diagram illustrating a signal path flow of an example ADC 10B. ADC 10B of FIG. 2B conforms substantially with ADC 10A of FIG. 2A. However, ADC 10B does not include input capacitance Cin 35 and feedback capacitance Cfb 33 to produce a desired gain. Instead, DAC 20 is configured to provide the desired gain internally, thereby eliminating the need for Cin 35 and Cfb 33. Although shown as summing node 36 outside of mixer amplifier 14, in some embodiments, summing node 36 may actually be implemented within mixer amplifier 14.

Figure 3A:
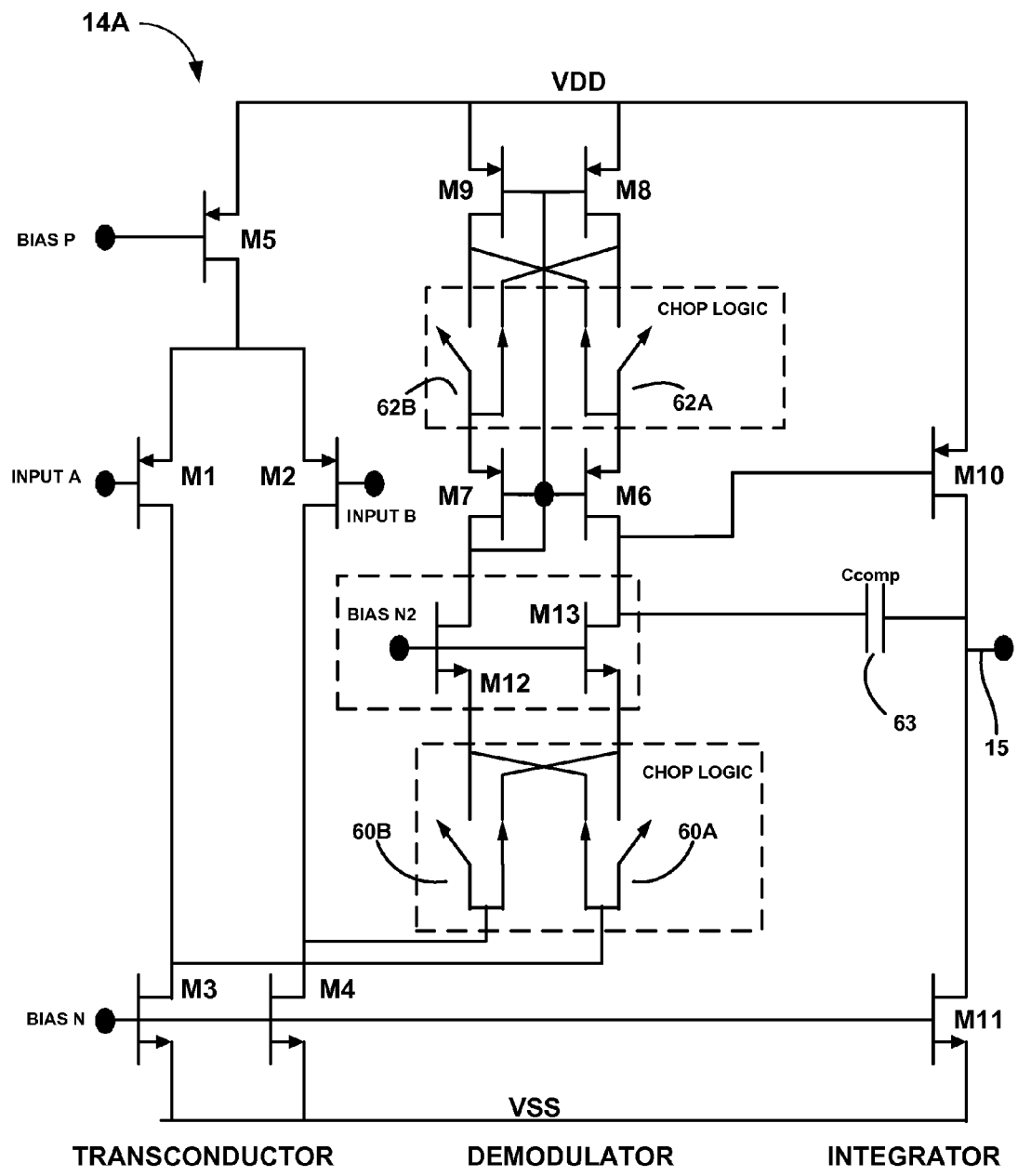
FIG. 3A is a circuit diagram illustrating an example mixer amplifier suitable for use in the chopper-stabilized ADC of FIG. 1.

FIG. 3A is a circuit diagram illustrating an example embodiment of mixer amplifier 14A of ADC 10 in greater detail. As previously described, mixer amplifier 14A introduces noise, such as RTS (popcorn) noise, 1/f noise, and offset, into modulated signal 13. Mixer amplifier 14A amplifies this signal to produce an amplified signal, demodulates the amplified signal, and integrates the demodulated signal to filter out frequency components that are outside of the measurement band (baseband). In this way, mixer amplifier 14A substantially eliminates noise from the demodulated signal to generate stable, low noise signal 13.

In the example of FIG. 3A, mixer amplifier 14A is a modified folded-cascode amplifier with switching at low impedance nodes. The modified folded-cascode architecture allows the currents to be partitioned to maximize noise efficiency. In general, the folded cascode architecture is modified in FIG. 3A by adding two sets of switches. One set of switches is illustrated in FIG. 3A as switches 60A and 60B (collectively referred to as "switches 60") and the other set of switches includes switches 62A and 62B (collectively referred to as "switches 62").

Switches 60 are driven by chop logic to support the chopping of the amplified signal for demodulation at the chop frequency. In particular, switches 60 demodulate the amplified signal and modulate RTS (popcorn) noise, 1/f noise, and front-end offsets. Switches 62 are embedded within a self-biased cascode mirror formed by transistors M6, M7, M8 and M9, and are driven by chop logic to up-modulate the low frequency errors from transistors M8 and M9. Low frequency errors in transistors M6 and M7 are attenuated by source degeneration from transistors M8 and M9. The demodulated signal, i.e., demodulated signal 43 in FIG. 2A and FIG. 2B, is at baseband, allowing an integrator formed by transistor M10 and capacitor 63 (Ccomp) to stabilize feedback path 16 (not shown in FIG. 3A) and filter modulated offsets.

Mixer amplifier 14A has three main blocks: a transconductor, a demodulator, and an integrator. The core is similar to a folded cascode. In the transconductor section, transistor M5 is a current source for the differential pair of input transistors M1 and M2. In some embodiments, transistor M5 may pass approximately 800 nA, which is split between transistors M1 and M2, e.g., 400 nA each. Transistors M1 and M2 are the inputs to amplifier 14A. Small voltage differences steer differential current into the drains of transistors M1 and M2 in a typical differential pair way. Transistors M3 and M4 serve as low side current sinks, and may each sink roughly 500 nA, which is a fixed, generally nonvarying current. Transistors M1, M2, M3, M4 and M5 together form a differential transconductor.

In this example, approximately 100 nA of current is pulled through each leg of the demodulator section. The AC current at the chop frequency from transistors M1 and M2 also flows through the legs of the demodulator. Switches 60 alternate the current back and forth between the legs of the demodulator to demodulate the measurement signal back to baseband, while the offsets from the transconductor are up-modulated to the chopper frequency. As discussed previously, transistors M6, M7, M8 and M9 form a self-biased cascode mirror, and make the signal single-ended before passing into the output integrator formed by transistor M10 and capacitor 63 (Ccomp). Switches 62 placed within the cascode (M6-M9) upmodulate the low frequency errors from transistors M8 and M9, while the low frequency errors of transistor M6 and transistor M7 are suppressed by the source degeneration they see from transistors M8 and M9. Source degeneration also keeps errors from Bias N2 transistors 66 suppressed. Bias N2 transistors M12 and M13 form a common gate amplifier that presents a low impedance to the chopper switching and passes the signal current to transistors M6 and M7 with immunity to the voltage on the drains.

The output DC signal current and the upmodulated error current pass to the integrator, which is formed by transistor M10, capacitor 63, and the bottom NFET current source transistor M11. Again, this integrator serves to both stabilize the feedback path and filter out the upmodulated error sources. The bias for transistor M10 may be approximately 100 nA, and is scaled compared to transistor M8. The bias for lowside NFET M11 may also be approximately 100 nA (sink). As a result, the integrator is balanced with no signal. If more current drive is desired, current in the integration tail can be increased appropriately using standard integrate circuit design techniques. Various transistors in the example of FIG. 3A may be field effect transistors (FETs), and more particularly CMOS transistors. In this manner, mixer amplifier 14A receives a differential input (e.g., input A and input B) and generates a single-ended output (e.g., output 15).

Figure 3B:
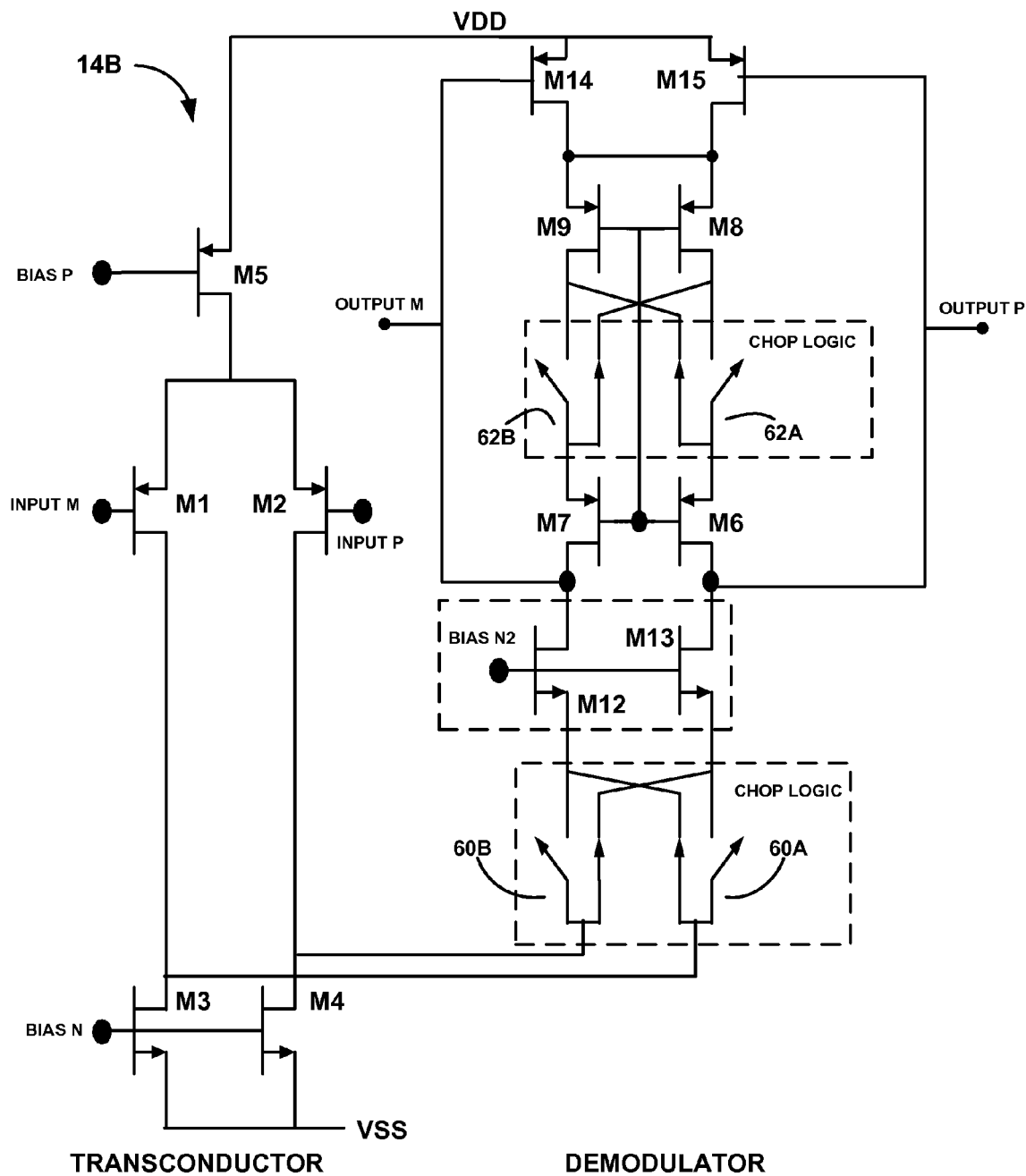
FIG. 3B is a circuit diagram illustrating another example mixer amplifier suitable for use in the chopper-stabilized ADC of FIG. 1.

FIG. 3B is a circuit diagram illustrating another example embodiment of mixer amplifier 14B for use in ADC 10. Mixer amplifier 14B conforms substantially to mixer amplifier 14A of FIG. 3A. However, mixer amplifier 14B receives a single-ended inputs (e.g., input M and input P) and generates a differential output (output M and output P). The single-ended inputs may be received from front end 12 and negative feedback loop 16, respectively.

Mixer amplifier 14B does not include the integrator block formed by transistor M10, capacitor 63, and the bottom NFET current source transistor M11 of FIG. 3A. Instead, mixer amplifier 14B includes additional transistors M14 and M15 inserted between VDD and transistors M9 and M8, respectively. The gate of transistor M14 and the drain of transistor M7 are coupled to form differential output M while the gate of transistor M15 and the drain of transistor M6 are coupled to form differential output P. Integration may be performed by adding a capacitor on each of the output nodes. These capacitors integrate the current from the tranconductance amplifier to generate the integrated output.

FIG. 4 is a block diagram illustrating an example of ADC 10 in greater detail. It should be understood that FIG. 4 is merely exemplary and should not be considered limiting of the invention as described in this disclosure in any way. Rather, it is the purpose of FIG. 4 to provide an overview that is used to describe the operation of ADC 10 in greater detail. This overview is used as a framework for describing the previously mentioned example embodiments with respect to the detailed circuit diagrams provided in this disclosure.

In the example of FIG. 4, front end 12 outputs a modulated input signal that is combined with a negative feedback signal 21 provided by DAC-based feedback path 16 to produce modulated input signal 13 that carries the signal of interest at a carrier frequency. As previously described, front end 12 may be, for example, a continuous time switched capacitor network that modulates (chops) an input signal from a physiological sensor, such as be a set of electrodes, an accelerometer, a pressure sensor, a voltage sensor or other sensor that outputs a voltage signal. In particular, front end 12 may generate a signal proportional to physiological signals such as, ECG signals, EMG signals, EEG signals, or other signals. The signal generated by front end 12 is a low frequency signal within a range of approximately 0 Hz to approximately 100 Hz, and may be less than approximately 2 Hz, and in some cases less than approximately 1 Hz. It should be understood, however, that front end 12 may be any component or combination of components that produces a modulated input signal. As described above, the signal produced by front end 12 may be either a differential signal or a single-ended signal.

Using an example in which a physiological sensor is coupled to the inputs of ADC 10, the modulator in front end 12 may, in the case of a differential configuration, include a differential set of switches, e.g., CMOS switches, that are toggled between the outputs of the physiological sensor to modulate (chop) an amplitude of the input signal. Clock 78 supplies the clock signal that the modulator in the front end 12 and demodulator 86 in mixer amplifier 14 use to modulate the differential input signal at the carrier (chop) frequency. At one end, the switches are cross coupled to each other and toggle between the output terminals of the sensor to reject common mode signals and operate as continuous time process, i.e., a non-sampling process. The switches are coupled at the other end to input capacitors of mixer amplifier 14 to form a continuous time switched capacitor network. In this way, front end 12 amplitude modulates (chops) the differential input signal at the inputs to mixer amplifier 14. Consequently, the modulated differential input signal produced by front end 12 is a square wave with a frequency equal to the carrier frequency. A circuit diagram for this example embodiment is provided in FIG. 5A. Although the example front end described above has a differential architecture that generates a differential modulated signal, front end 12 may generate a single-ended modulated signal as described further in FIG. 5B.

Mixer amplifier 14 is illustrated in FIG. 4 as including amplifier 40, modulator 42, and integrator 44 and may be implemented using a modified folded cascode architecture, e.g., as illustrated in FIG. 3A or FIG. 3B. Accordingly, mixer amplifier 14 may use chopper stabilization to produce stable, low noise output signal 15 as previously described.

In the example embodiment illustrated in FIG. 4, ADC circuitry 18 includes comparator 46, compensator 47 which aids in stabilizing feedback path 16, and up/down counter 48 which is controlled by comparator 46 as previously described in FIG. 2. By counting up or down based on the comparison of signals 15 and Vref 45, ADC circuitry 18 adjusts digital signal 19 to provide a good (accurate) approximation of analog input signal 2.

In FIG. 4, ADC 10 includes negative feedback path 16. Negative feedback path 16 provides negative feedback at the input to mixer amplifier 14, as previously described, to keep the signal change small. Negative feedback path 16 modulates signal 21 according to a clock provided by clock 78 or a clock generated from clock 78. Moreover, negative feedback path 16 modulates signal 21 with a reference voltage provided by reference and bias generator 94.

In embodiments in which mixer amplifier 14 has a differential input, negative feedback path 16 may include two symmetrical feedback path branches to provide feedback to respective positive and negative differential inputs of mixer amplifier 14, i.e., to provide a differential-to-single conversion. In this case, to ensure that a negative feedback path exists in negative feedback path 16 at all times, the chop frequency applied to the negative feedback path branches of feedback path 16 should be 180 degrees out of phase with each other with one of the feedback paths synchronous with the modulators located in front end 12. In this way, one of the feedback path branches of negative feedback path 16 is applying negative feedback during each half of the clock cycle. As a result, the differential signals at the input of mixer amplifier 14 are small and centered about the reference voltage.

For a mixer amplifier 14 that includes single-ended inputs, negative feedback path 16 may include a single feedback path that provided a negative (or inverted) input to mixer amplifier 14 and the input signal may provide a positive or (non-inverted) input to mixer amplified 14. Regardless of whether the feedback is differential or single-ended, negative feedback 16 substantially eliminates the glitching in output signal 15 that would otherwise result from the limited bandwith of mixer amplifier 14 operating at very low power.

ADC 10 may be implemented with one or more clocks to supply clock signals to front end 12, mixer amplifier 14, feedback path 16, and up/down converter 48. For example, since the clock signals that drive front end 12, mixer amplifier 14, and feedback path 16, all operate at the same frequency, the signals may be provided by a single clock. In this case, additional circuitry may be provided to drive the modulator in feedback path 16 and to derive the clock signal to drive up/down counter 48. Alternatively, two clocks may be used, with one clock driving front end 12, mixer amplifier 14, and feedback path 16, and the other driving up/down counter 48.

Reference and bias generator 80 supplies bias voltages to front end 12, mixer amplifier 14, feedback path 16, and comparator 46. When front end 12 includes a physiological sensor, reference and bias generator 80 may supply reference voltages that drive the physiological sensor. With respect to mixer amplifier 14, reference and bias generator 80 may supply bias voltages for biasing the transistors as shown in FIG. 3A and FIG. 3B. The reference voltages that are mixed with signal 21 and the signals in feedback path 16 as previously described may also be supplied by reference and bias generator 80. Bias voltages of 0 volts to 1.2 volts (bandgap) or 0 volts to 0.6 volts (half bandgap) may be used as bias points.

Figure 5A:
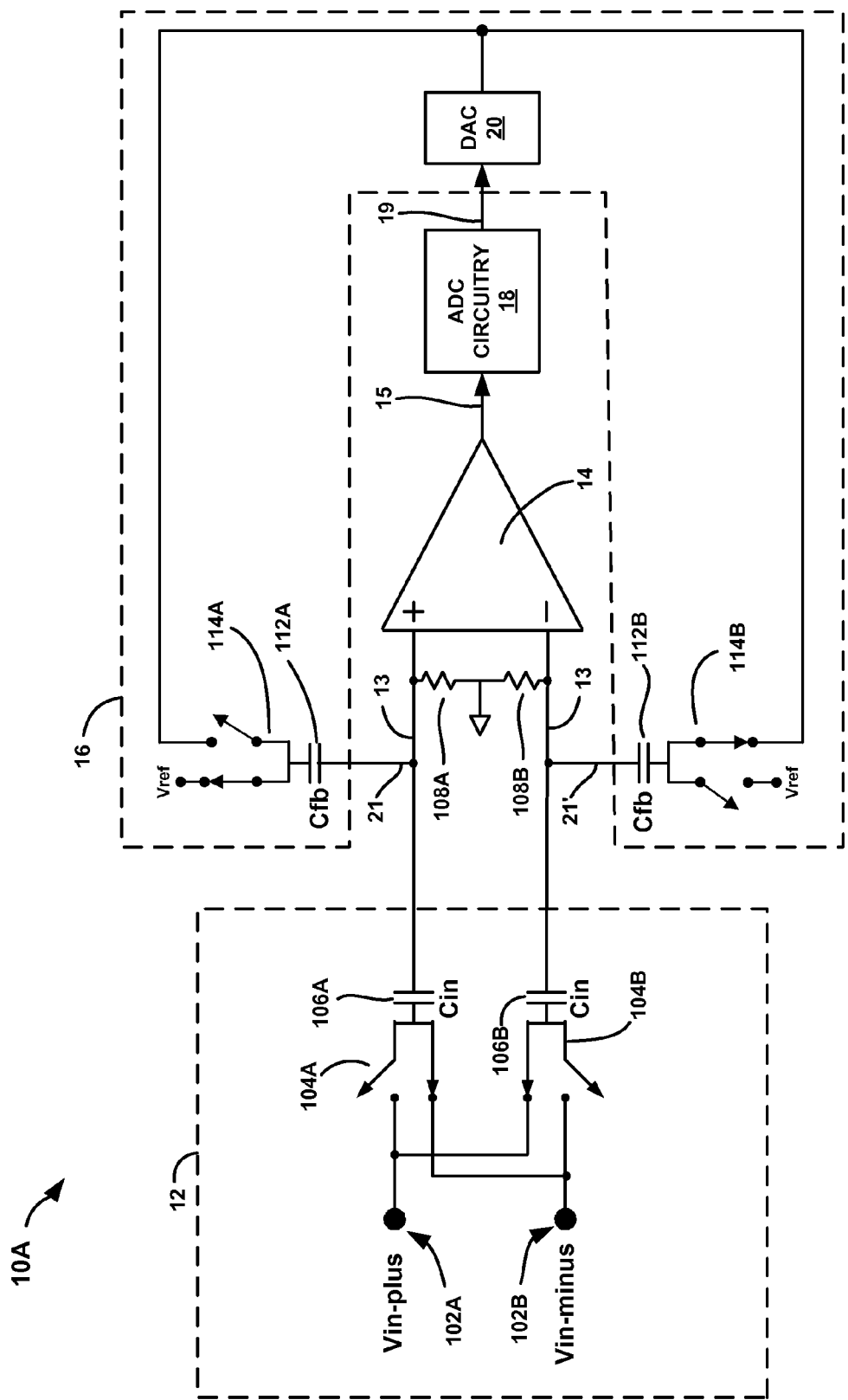
FIG. 5A is a circuit diagram illustrating an example embodiment of the chopper-stabilized ADC of FIG. 1.

FIG. 5A is a circuit diagram illustrating an example embodiment of ADC 10A. In FIG. 5A, ADC 10A includes inputs 102A and 102B (collectively referred to as "inputs 102"). In an example embodiments, a physiological sensor may generate a differential voltage across inputs 102, i.e., voltages Vin-plus and Vin-minus, respectively. The physiological sensor may, for example, be an accelerometer, a pressure sensor, a force sensor, a gyroscope, a humidity sensor, a pair of electrodes, or other sensor that translates biophysical signals to a differential electrical voltage across inputs 102. In some embodiments, inputs 102A, 102B may be derived from the output of a sensing circuit that includes a sensor and instrumentation amplifier circuitry for amplifying filtering a signal generated by the sensor.

In the example of FIG. 5A, inputs 102A and 102B are connected to capacitors 106A and 106B (collectively referred to as "capacitors 106") through switches 104A and 104B (collectively referred to as "switches 104), respectively. Switches 104 are driven by a clock signal provided by a system clock (not shown) and are cross-coupled to each other to reject common-mode signals. Capacitors 106 are coupled at one end to a corresponding one of switches 104 and to a corresponding input of mixer amplifier 116 at the other end. In particular, capacitor 106A is coupled to the positive input of mixer amplifier 116, and capacitor 106B is coupled to the negative input of amplifier 116, providing a differential input. Capacitors 106 are switched at the modulation frequency to chop the signal at inputs 102, which may be derived from the output of a sensor or the output of sensor circuitry that amplifies and filters the output of the sensor. In either case, ADC 10A converts the analog input signal to a digital signal 19.

In FIG. 5A, switches 104 and capacitors 106 form front end 12. Accordingly, switches 104 correspond to modulator 30 in FIG. 2A and FIG. 2B and front end 12 operates as a continuous time switched capacitor network as previously described. Switches 104 toggle between an open state and a closed state in which inputs 102 are coupled to capacitors 106 at a clock frequency to modulate (chop) the signal at inputs 102, e.g., analog input signal 2, to the carrier (clock) frequency. As previously described, signal at inputs 102 may be a low frequency signal within a range of approximately 0 Hz to approximately 100 Hz. The carrier frequency may be within a range of approximately 4 kHz to approximately 10 kHz. Hence, the low frequency sensor output is chopped to the higher chop frequency band.

Switches 104 toggle in-phase with one another to provide a differential input. During a first phase of the clock signal, switch 104A connects sensor output 102B to capacitor 106A and switch 104B connects sensor output 102A to capacitor 106B. During a second phase, switches 104 change state such that switch 104A couples port 102A to capacitor 106A and switch 104B couples port 102B to capacitor 106B. Switches 104 synchronously alternate between the first and second phases to modulate the differential voltage at inputs 102 at the carrier frequency. The resulting chopped differential signal is applied across capacitors 106.

Resistors 108A and 108B (collectively referred to as "resistors 108") provide a DC conduction path that controls the voltage bias at the input of mixer amplifier 14. In other words, resistors 108 may be selected to provide an equivalent resistance that is used to keep the bias impedance high. Resistors 108 may, for example, be selected to provide a 5 GΩ equivalent resistor, but the absolute size of the equivalent resistor is not critical to the performance of ADC 10A. In general, increasing the impedance improves the noise performance and rejection of harmonics, but extends the recovery time from an overload. To provide a frame of reference, a 5 GΩ equivalent resistor results in a referred-to-input (RTI) noise of approximately 20 nV/rt Hz with an input capacitance (Cin) of approximately 25 pF. In light of this, it may be desirable to keep the impedance high to reject high frequency harmonics that can alias into the signal chain due to settling at the input nodes of mixer amplifier 14 during each half of a clock cycle.

It is important to note that resistors 108 are merely exemplary and serve to illustrate one of many different biasing schemes for controlling the signal input to mixer amplifier 116. In fact, the biasing scheme is flexible because the absolute value of the resulting equivalent resistance is not critical. In general, the time constant of resistor 108 and input capacitor 106 may be selected to be approximately 100 times longer than the reciprocal of the chopping frequency.

Mixer amplifier 14 may produce noise and offset in the differential signal applied to its inputs. For this reason, front end 12 chops the signal at inputs 102 to place the signal of interest in a different frequency band from the noise and offset. Then, mixer amplifier 14 chops the amplified signal a second time to demodulate the signal of interest down to baseband while modulating the noise and offset up to the chop frequency band. In this manner, ADC 10A maintains substantial separation between the noise and offset and the signal of interest. Mixer amplifier 14 and feedback path 16 process the noisy modulated input signal to achieve a stable measurement of the low frequency signal at inputs 102 while operating at low power.

As previously described, operating at low power tends to limit the bandwidth of mixer amplifier 14 and creates distortion (ripple) in the output signal. Mixer amplifier 14 and feedback path 16 operate in the previously described manner. In this way, mixer amplifier 14 and feedback path 16 substantially eliminate the dynamic limitations of chopper stabilization through a combination of chopping at low-impedance nodes and AC feedback, respectively.

In FIG. 5A, mixer amplifier 14 is represented with the circuit symbol for an amplifier in the interest of simplicity. However, it should be understood that mixer amplifier 14 may be implemented in accordance with the circuit diagram provided in FIG. 3A or FIG. 3B. Consequently, mixer amplifier 14 provides synchronous demodulation with respect to front end 12 and substantially eliminates RTS (popcorn) noise, 1/f noise, and offset from the signal at the inputs to mixer amplifier 14 to produce a stable, low noise signal, i.e., signal 15, that is an amplified representation of the signal at inputs 102.

ADC circuitry 18 is represented in FIG. 5A as a functional block due to limitations of space. As previously described, ADC circuitry 18 may be implemented using a comparator, a compensator that aids in stabilizing feedback path 16, and an up/down converter controlled by the comparator. Other configurations for implementing ADC circuitry 18 may be used to implement ADC circuitry and may become apparent to those skilled in the art upon consideration of this disclosure, and are within the scope of the invention as broadly described in this disclosure.

DAC 20 generates analog signal 21 as an approximation of the signal at inputs 102 using the digital value 19 generated by ADC circuitry 18 and forms a portion of feedback path 16. Without the negative feedback provided by feedback path 16, the output of mixer amplifier 14 could include spikes superimposed on the desired signal because of the limited bandwidth of the amplifier at low power. However, the negative feedback provided by feedback path 16 suppresses these spikes so that the output of mixer amplifier 14 (signal 15) in steady state is an amplified representation of the differential voltage at inputs 102 with very little noise. Because signal 15 is a stable, low noise signal, ADC circuitry 18 can generate digital signal 19 with increased accuracy in approximating the analog input signal. Consequently, ADC 10A may reduce oversensing that might result in withholding needed therapy or providing therapy when it is not needed.

Feedback path 16 in FIG. 5A may include two feedback paths that provide a single-ended to differential interface. The top branch of feedback path 16 modulates the output of DAC 20 to provide negative feedback to the positive input terminal of mixer amplifier 14. This feedback path branch includes capacitor 112A and switch 114A. Similarly, the bottom feedback path branch of feedback path 16 includes capacitor 112B and switch 114B that modulate the output of mixer amplifier 14 to provide negative feedback to the negative input terminal of mixer amplifier 14. The feedback path branches produce signals 21 and 21'. Capacitors 112A and 112B are connected at one end to switches 114A and 114B, and at the other end to the positive and negative input terminals of mixer amplifier 116, respectively.

Switches 114A and 114B toggle between a reference voltage (Vref) and the output of mixer amplifier 14 to place a charge on capacitors 112A and 112B, respectively. The reference voltage may be, for example, a mid-rail voltage between a maximum rail voltage of amplifier 14 and ground. For example, if the amplifier circuit is powered with a source of 0 to 2 volts, then the mid-rail Vref voltage may be on the order of 1 volt. Importantly, switches 114A and 114B should be 180 degrees out of phase with each other to ensure that a negative feedback path exists during each half of the clock cycle. One of switches 114 should also be synchronized with mixer amplifier 14 so that the negative feedback suppresses the amplitude of the input signal to mixer amplifier 14 to keep the signal change small in steady state. By keeping the signal change small and switching at low impedance nodes of mixer amplifier 14, e.g., as shown in the circuit diagram of FIG. 3, the only significant voltage transitions occur at switching nodes. Consequently, glitching (ripples) is substantially eliminated or reduced at the output of mixer amplifier 14.

Switches 104 and 114, as well as the switches at low impedance nodes of mixer amplifier 116, may be CMOS SPDT switches. CMOS switches provide fast switching dynamics that enables switching to be viewed as a continuous process. The transfer function of ADC 10 may be defined by the transfer function provided in equation (1) below, where Vout is the voltage of the output of mixer amplifier 14, Cin is the capacitance of input capacitors 106, $\Delta$Vin is the differential voltage at the inputs to mixer amplifier 14, Cfb is the capacitance of feedback capacitors 112, and Vref is the reference voltage that switches 114 mix with the output of mixer amplifier 14.

$$Vout = Cin(\Delta Vin)/Cfb + Vref \qquad (1)$$

From equation (1), it is clear that the gain of ADC 10A is set by the ratio of input capacitors Cin and feedback capacitors Cfb, i.e., capacitors 106 and capacitors 112. The ratio of Cin/Cfb may be selected to be on the order of 100. Capacitors 112 may be poly-poly, on-chip capacitors or other types of MOS capacitors and should be well matched, i.e., symmetrical.

Although not shown in FIG. 5A, mixer amplifier 14 may include shunt feedback paths for auto-zeroing amplifier 14. The shunt feedback paths may be used to quickly reset amplifier 14. An emergency recharge switch also may be provided to shunt the biasing node to help reset the amplifier quickly. The function of input capacitors 106 is to up-modulate the low-frequency differential voltage at inputs 102 and reject common-mode signals. As discussed above, to achieve up-modulation, the differential inputs are connected to sensing capacitors 106A, 106B through SPDT switches 104. The phasing of the switches provides for a differential input to the ac transconductance mixing amplifier 14. These switches 104 operate at the clock frequency, e.g., 4 kHz. Because the sensing capacitors 106 toggle between the two inputs, the differential voltage is up-modulated to the carrier frequency while the low-frequency common-mode signals are suppressed by a zero in the charge transfer function. The rejection of higher-bandwidth common signals relies on this differential architecture and good matching of the capacitors.

Figure 5B:
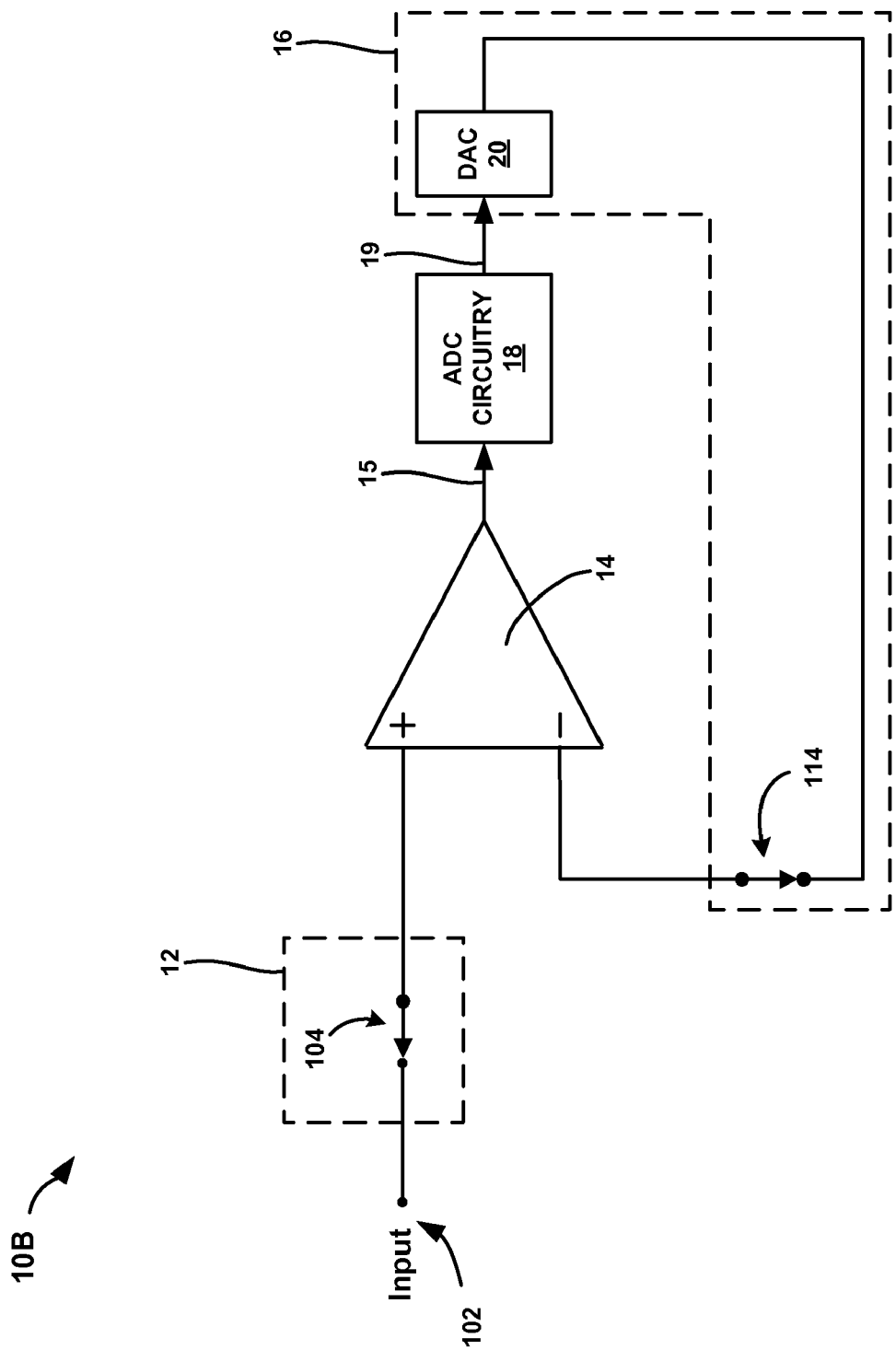
FIG. 5B is a circuit diagram illustrating another example embodiment of the chopper-stabilized ADC of FIG. 1.

FIG. 5B is a circuit diagram illustrating another example embodiment of ADC 10B. ADC 10B of FIG. 5B conforms substantially with ADC 10A of FIG. 5A. However, ADC 10B of FIG. 5B includes front end 12 that produces a single ended input for a positive (non-inverted) input of mixer amplifier 14 instead of a front end that produces a differential input for a differential input mixer amplifier. In particular, front end 12 includes a switch 104 that is driven by a clock signal provided by a system clock (not shown). Switch 104 may, for example, correspond to modulator 30 in FIG. 2A and FIG. 2B. Switch 104 toggles between an open state and a closed state at a clock frequency to modulate (chop) the signal at input 102, e.g., analog input signal 2, to the carrier (clock) frequency. The chopped input is provided to the positive input of mixer amplifier 14.

Moreover, DAC 20 of ADC 10B provides only a single branch feedback path 16 to mixer amplifier 14 instead of a single-ended to differential interface. In particular, provides a single-ended chopped input to a negative (inverting) input of mixer amplifier 14. To this end, feedback path 16 includes a switch 114, like switch 104, is driven by a clock signal to toggle between an open state and a closed state to modulate (chop) the feedback signal from DAC 20, e.g., reconstructed signal 21.

Figure 6:
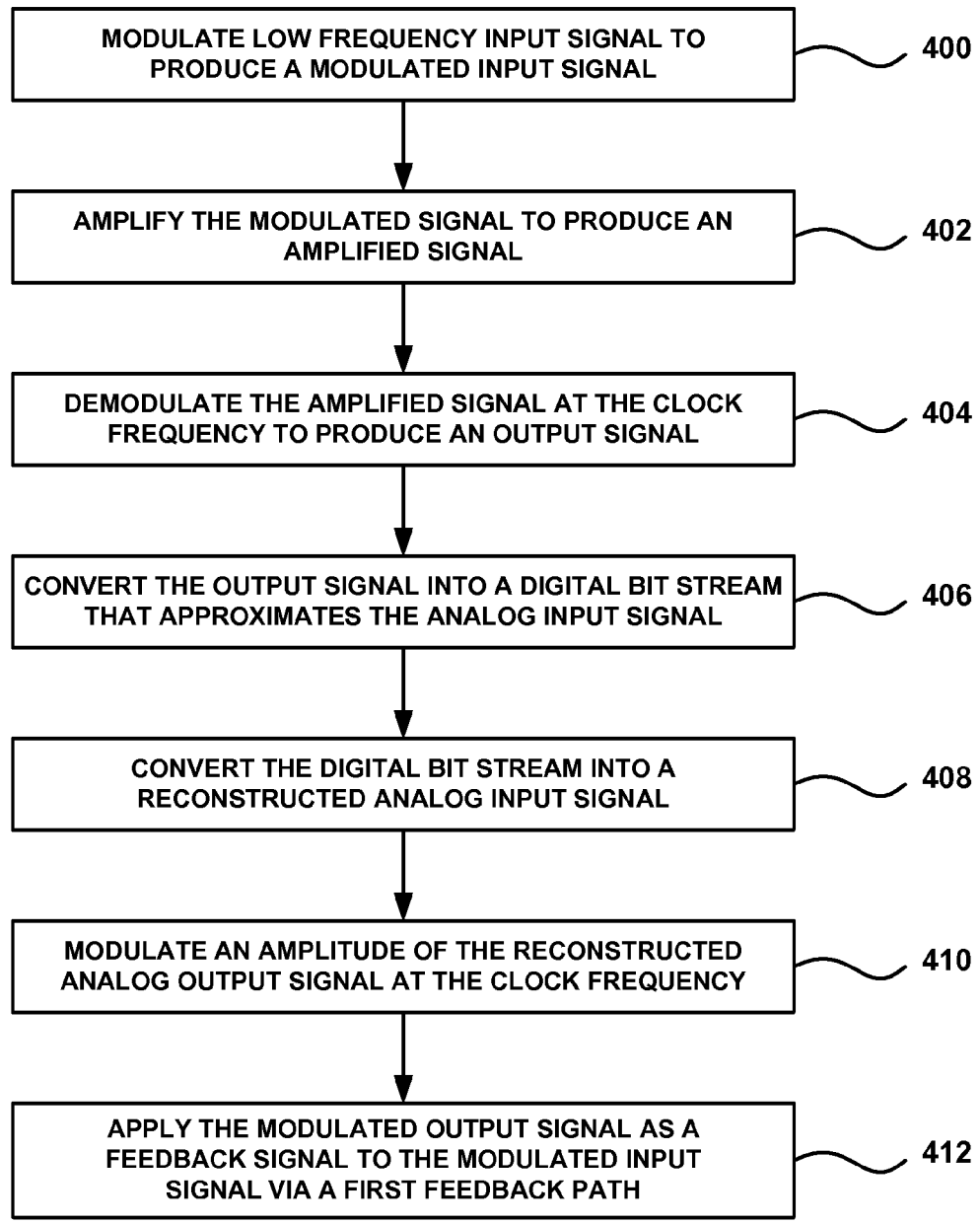
FIG. 6 is a flow diagram illustrating a method utilized by an ADC to convert a low frequency analog input signal into a digital signal.

FIG. 6 is a flow diagram illustrating a method utilized by a chopper-stabilized ADC. The method shown in FIG. 6 may be implemented using circuitry as described in this disclosure. As shown in FIG. 6, the method may comprise modulating a low frequency analog input signal to produce a modulated input signal (400), amplifying the modulated signal to produce an amplified signal (402), demodulating the amplified signal at the clock frequency to produce an output signal (404), converting the output signal into a digital value that approximates the analog input signal (406), converting the digital value into a reconstructed analog output signal (408), modulating an amplitude of the reconstructed analog output signal at the clock frequency (410), and applying the modulated output signal as a feedback signal to the modulated input signal via a first feedback path (412).

Figure 7:
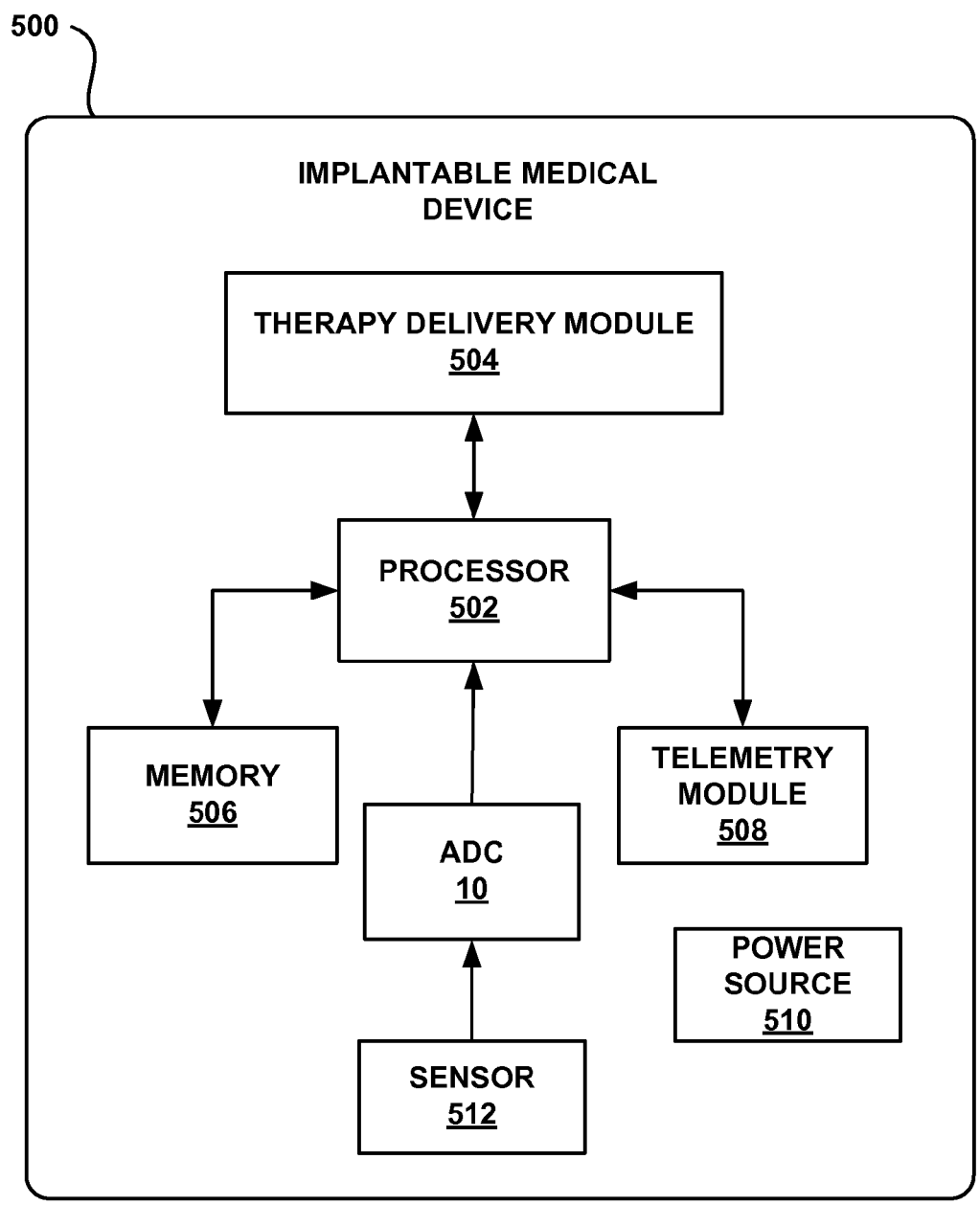
FIG. 7 is a block diagram of an implantable medical device (IMD) including an ADC in accordance with an embodiment of this disclosure.

FIG. 7 is a block diagram of an implantable medical device (IMD) 500 including an ADC 10 in accordance with an embodiment of this disclosure. In the example of FIG. 1, IMD 120 includes processor 502, therapy delivery module 504, memory 506, telemetry module 508, power source 510, sensor 512, and ADC 10. ADC 10 is chopper-stabilized, as described in this disclosure, to substantially reduce or eliminate noise and offset from an output signal produced by the ADC. IMD 500 may be dedicated to therapy, such as delivery of electrical stimulation or drug delivery. To that end, IMD 500 includes therapy delivery module 504 in the example of FIG. 7. Alternatively, IMD 500 may be dedicated to sensing or a combination of therapy and sensing. In either case, IMD 500 makes use of sensed signals from sensor 512.

Sensor 512 may include any type of sensor or combination of sensors. For example, sensor 512 may be a pressure sensor, accelerometer, activity sensor, impedance sensor, electrical signal sensor or other sensor configured to monitor heart sounds, brain signals, and/or other physiological signals. Although illustrated in FIG. 7 as contained within IMD 500, a portion of sensor 512 may be located outside of IMD 500. For example, a sensor transducer or one or more electrodes may be located on a distal tip of a lead implanted at a target site within the patient and electrically coupled to IMD 500 via conductors. Alternatively, a sensor transducer or one or more electrodes may be provided on or within a housing of IMD 500. For example, an accelerometer may be provided within an IMD housing or within a lead that extends from the IMD. To sense electrical signals, sensor 512 may include two or more electrodes arranged on a lead, an electrode on a lead and an electrode on an IMD housing, two or more electrodes arranged on an IMD housing, or other electrode arrangements. Sensor circuitry associated with sensor 130 may be provided within sensor 512 in the housing of IMD 500.

In general, sensor 512 provides a measurement of a physiological signal or parameter by translating a signal or parameter to an output voltage or current. The output of sensor 512 may be received by processor 502 via ADC 10. Processor 502 may apply additional processing, e.g., convert the output to digital values for processing, prior to storing the values in memory 506, and/or transmitting the values to an external programmer via telemetry module 508. Telemetry module 508 may include a receiver and a transmitter.

Processor 502 may also control delivery of therapy to the patient based on the output of sensor 512. IMD 500 may deliver therapy to a patient via one or more therapy elements, which may be within or on, or extend from, a housing associated with IMD 500. In other embodiments, IMD 500 may be dedicated to sensing and may not include therapy delivery module 504. Therapy delivery elements may be electrodes carried on one or more implantable leads, electrodes on the housing of IMD 500, one or more fluid delivery devices, or any combination thereof. For delivery of electrical stimulation, therapy delivery module 504 may include an implantable stimulation generator or other stimulation circuitry that generates electrical signals, e.g., pulses or substantially continuous signals, such as sinusoidal signals, to the patient via at least some of the electrodes that form therapy elements under the control of processor 502.

Stimulation energy generated by therapy delivery module 504 may be formulated as stimulation energy for treatment of any of a variety of cardiac or neurological disorders, or disorders influenced by patient neurological response. Example stimulation therapies include cardiac pacing, cardiac defibrillation, deep brain stimulation (DBS), spinal cord stimulation (SCS), peripheral nerve field stimulation (PNFS), pelvic floor stimulation, gastrointestinal stimulation, muscle stimulation, and the like.

Therapy delivery module 504, processor 502, telemetry module 508, memory 506, sensor 512 and ADC 10 may receive operating power from power source 510. Power source 510 may take the form of a small, rechargeable or non-rechargeable battery, or an inductive power interface that transcutaneously receives inductively coupled energy. In the case of a rechargeable battery, power source 510 similarly may include an inductive power interface for transcutaneous transfer of recharge power.

In embodiments in which one or more fluid delivery devices are part of therapy elements associated with therapy delivery module 504, the therapy delivery module may include one or more fluid reservoirs and one or more pump units that pump fluid from the fluid reservoirs to the target site through the fluid delivery devices. The fluid reservoirs may contain a drug or mixture of drugs. The fluid reservoirs may provide access for filling, e.g., by percutaneous injection of fluid via a self-sealing injection port. The fluid delivery devices may comprise, for example, catheters that deliver, i.e., infuse or disperse, drugs from the fluid reservoirs to the same or different target sites.

Processor 502 may include a microprocessor, microcontroller, digital signal processor (DSP), application specific integrated circuit (ASIC), field programmable gate array (FPGA), discrete logic circuitry, or a combination of such components. Processor 502 may be programmed to control delivery of therapy according to a selected parameter set stored in memory 506. Specifically, processor 502 controls therapy delivery module 504 to deliver electrical stimulation, drug therapy, or a combination of both. For example, processor 502 may control which drugs are delivered and the dosage of the drugs delivered.

Processor 502 may also control therapy delivery module 504 to deliver electrical stimulation with pulse amplitudes, pulse widths, and frequencies (i.e., pulse rates) specified by the programs of the selected parameter set. Processor 502 may also control therapy delivery module 504 to deliver electrical stimulation or drugs according to a different program of the parameter set. In some embodiments, processor 502 may control therapy delivery module 504 to deliver a substantially continuous stimulation waveform rather than pulsed stimulation.

Memory 506 may store parameter sets that are available to be selected by the patient for delivery of electrical stimulation and/or drug therapy. Memory 506 may also store schedules. Memory 506 may include any combination of volatile, non-volatile, removable, magnetic, optical, or solid state media, such as read-only memory (ROM), random access memory (RAM), electronically-erasable programmable ROM (EE-PROM), flash memory, or the like.

Processor 502 may control telemetry module 126 to exchange information with an external programmer, such as a clinician programmer and/or patient programmer, by wireless telemetry. Processor 502 may control telemetry module 508 to communicate with the external programmer on a continuous basis, at periodic intervals, or upon request from the programmer. In addition, in some embodiments, telemetry module 508 may support wireless communication with one or more wireless sensors that sense physiological signals and transmit the signals to IMD 120.

Telemetry module 508 may operate as a transceiver that receives telemetry signals from an external programmer and transmits telemetry signals to an external programmer. A portion of telemetry module 508 is configured operate as a transmitter to transmit signals from IMD 500 to an external programmer or to another IMD or external medical device.

A chopper-stabilized ADC as described in this disclosure may be useful in a variety of applications. Specifically, the ADC may be useful in applications that operate at low frequency with very low power. For example, the invention may be applied to support to support sensing relating to therapies for a variety of symptoms or conditions such as cardiac arrhythmia, cardiac fibrillation, chronic pain, tremor, Parkinson's disease, epilepsy, urinary or fecal incontinence, sexual dysfunction, obesity, or gastroparesis, and may provide information useful in controlling electrical stimulation or drug delivery to a variety of tissue sites, such as the heart, the brain, the spinal cord, pelvic nerves, peripheral nerves, or the gastrointestinal tract of a patient.

Hence, an ADC as described in this disclosure may be integrated with, housed in, coupled to, or otherwise associated with an external or implantable medical device, such as a cardioverter/defibrillator, spinal cord stimulator, pelvic nerve stimulator, deep brain stimulator, gastrointestinal stimulator, peripheral nerve stimulator, or muscle stimulator, and also may be used in conjunction with implantable or external drug delivery devices. For example, an ADC and/or associated sensing and measurement circuitry may reside within an implantable medical device housing or a lead or catheter coupled to such a device.

The ADC may be used in conjunction with different therapeutic applications, such as cardiac stimulation, deep brain stimulation (DBS), spinal cord stimulation (SCS), pelvic stimulation for pelvic pain, incontinence, or sexual dysfunction, gastric stimulation for gastroparesis, obesity or other disorders, or peripheral nerve stimulation for pain management. Stimulation also may be used for muscle stimulation, e.g., functional electrical stimulation (FES) to promote muscle movement or prevent atrophy.

Various embodiments been described. These and other embodiments are within the scope of the following claims.

The invention claimed is:

1. A chopper-stabilized analog-to-digital converter (ADC) comprising:
    a first modulator that modulates an amplitude of an analog input signal at a frequency to produce a modulated input signal;
    a mixer amplifier that amplifies the modulated input signal to produce an amplified signal, demodulates the amplified signal at the frequency to produce a demodulated signal, and integrates the demodulated signal to produce an output signal;
    circuitry that converts the output signal into a digital value that approximates the analog input signal;
    circuitry that converts the digital value into a reconstructed analog output signal;
    a second modulator that modulates an amplitude of the reconstructed analog output signal at the frequency to produce a modulated output signal; and
    a feedback path that applies the modulated output signal as a feedback signal to the modulated input signal.

2. The ADC of claim 1, wherein a non-inverting input of the mixer amplifier inputs the modulated input signal from the first modulator and an inverting input of the mixer amplifier inputs the modulated output signal from the feedback path.

3. The ADC of claim 1, wherein the mixer amplifier is a differential input mixer amplifier that receives the modulated input signal as a differential input signal, and the feedback path includes a first feedback path branch coupled to a first input of the mixer amplifier and a second feedback path branch coupled to a second input of the mixer amplifier, and wherein the second modulator includes a modulator in the first feedback path branch and a modulator in the second feedback path branch that modulate the amplitude of the reconstructed analog output signal out of phase with one another.

4. The ADC of claim 3, wherein each of the first and second feedback path branches includes a feedback capacitance, each of the first and second inputs of the mixer amplifier is coupled to receive the differential input signal via an input capacitance, and a gain of the mixer amplifier is at least partially dependent on a ratio of the feedback capacitance to the input capacitance.

5. The ADC of claim 1, wherein the mixer amplifier includes:
    a third modulator that demodulates the amplified signal to a baseband frequency to produce the demodulated signal; and
    an integrator that integrates the demodulated signal produced by the third modulator.

6. The ADC of claim 1, further comprising a power source to power the amplifier, wherein the power source delivers less than approximately 2.0 microamps of electrical current to the amplifier during operation, and delivers a voltage of less than approximately 2.0 volts to the circuit, and wherein the input signal has a frequency of less than or equal to approximately 1.0 Hz.

7. The ADC of claim 1, wherein the mixer amplifier outputs a differential signal, and the circuitry that converts the output signal produced by the mixer amplifier into the digital value includes:
    a differential input comparator that produces a control signal with a first amplitude when an amplitude of the differential signal input to a positive input of the mixer amplifier is greater than an amplitude of the differential signal input to a negative input of the mixer amplifier;
    a compensator that suppresses the output signal produced by the mixer amplifier at frequencies lower than a high pass corner frequency; and
    an up/down counter that receives the control signal and increases an amplitude of the digital value when the control signal is received with the first amplitude, and decreases the amplitude of the digital value when the control signal is received with the second amplitude.

8. The ADC of claim 1, wherein the circuitry that converts the output signal produced by the mixer amplifier into the digital value includes:
- a comparator that produces a control signal with a first amplitude when an amplitude of the output signal is greater than a reference voltage and produces the control signal with a second amplitude when the amplitude of the output signal is less than the reference voltage;
- a compensator that suppresses the output signal produced by the mixer amplifier at frequencies lower than a high pass corner frequency; and
- an up/down counter that receives the control signal and increases an amplitude of the digital value when the control signal is received with the first amplitude, and decreases the amplitude of the digital value when the control signal is received with the second amplitude.

9. The ADC of claim 1, wherein the mixer amplifier amplifies and demodulates the modulated input signal prior to any integration of the modulated input signal.

10. The ADC of claim 1, wherein the mixer amplifier comprises a transconductor that amplifies the modulated input signal to produce the amplified signal.

11. An implantable medical device comprising:
- a physiological sensor that generates an input signal indicative of a physiological condition; and
- a chopper-stabilized analog-to-digital converter (ADC) comprising:
  - a first modulator that modulates an amplitude of the input signal at a frequency to produce a modulated input signal;
  - a mixer amplifier that amplifies the modulated input signal to produce an amplified signal, demodulates the amplified signal at the frequency to produce a demodulated signal, and integrates the demodulated signal to produce an output signal;
  - circuitry that converts the output signal into a digital value that approximates the analog input signal;
  - circuitry that converts the digital value into reconstructed analog output signal;
  - a second modulator that modulates an amplitude of the reconstructed analog output signal at the frequency to produce a modulated output signal; and
  - a feedback path that applies the modulated output signal as a feedback signal to the modulated input signal.

12. The device of claim 11, wherein a non-inverting input of the mixer amplifier inputs the modulated input signal from the first modulator and an inverting input of the mixer amplifier inputs the modulated output signal from the feedback path.

13. The device of claim 11, wherein the mixer amplifier is a differential input mixer amplifier that receives the modulated input signal as a differential input signal, and the feedback path includes a first feedback path branch coupled to a first input of the mixer amplifier and a second feedback path branch coupled to a second input of the mixer amplifier, and wherein the second modulator includes a modulator in the first feedback path branch and a modulator in the second feedback path branch that modulate the amplitude of the reconstructed analog output signal out of phase with one another.

14. The device of claim 13, wherein each of the first and second feedback path branches includes a feedback capacitance, each of the first and second inputs of the mixer amplifier is coupled to receive the differential input signal via an input capacitance, and a gain of the mixer amplifier is at least partially dependent on a ratio of the feedback capacitance to the input capacitance.

15. The device of claim 11, wherein the mixer amplifier includes:
- a third modulator that demodulates the amplified signal to a baseband frequency to produce the demodulated signal; and
- an integrator that integrates the demodulated signal produced by the third modulator.

16. The device of claim 11, further comprising a power source to power the device, wherein the power source delivers less than approximately 2.0 microamps of electrical current to the amplifier during operation, and delivers a voltage of less than approximately 2.0 volts to the circuit, and wherein the input signal has a frequency of less than or equal to approximately 1.0 Hz.

17. The device of claim 11, wherein the mixer amplifier outputs a differential signal, and the circuitry that converts the output signal produced by the mixer amplifier into the digital value includes:
- a differential input comparator that produces a control signal with a first amplitude when an amplitude of the differential signal input to a positive input of the mixer amplifier is greater than an amplitude of the differential signal input to a negative input of the mixer amplifier;
- a compensator that suppresses the output signal produced by the mixer amplifier at frequencies lower than a high pass corner frequency; and
- an up/down counter that receives the control signal and increases an amplitude of the digital value when the control signal is received with the first amplitude, and decreases the amplitude of the digital value when the control signal is received with the second amplitude.

18. The device of claim 11, wherein the circuitry that converts the output signal produced by the mixer amplifier into the digital value includes:
- a comparator that produces a control signal with a first amplitude when an amplitude of the output signal is greater than a reference voltage and produces the control signal with a second amplitude when the amplitude of the output signal is less than the reference voltage;
- a compensator that suppresses the output signal produced by the mixer amplifier at frequencies lower than a high pass corner frequency; and
- an up/down counter that receives the control signal and increases an amplitude of the digital value when the control signal is received with the first amplitude, and decreases the amplitude of the digital value when the control signal is received with the second amplitude.

19. The device of claim 11, wherein the sensor includes one of an accelerometer, a pressure sensor, and a voltage sensor.

20. The device of claim 11, wherein the sensor includes one of electrocardiogram (ECG), electromyogram (EMG), or electroencephalogram (EEG) sensor.

21. The device of claim 11, further comprising a processor that controls delivery of a therapy to a patient based on the digital signal from ADC.

22. The device of claim 11, wherein the implantable medical device includes one of a cardiac pacemaker, a cardiac defibrillator, an electrical neurostimulator, and an implantable drug delivery device.

23. The device of claim 11, wherein the mixer amplifier amplifies and demodulates the modulated input signal prior to any integration of the modulated input signal.

24. The device of claim 11, wherein the mixer amplifier comprises a transconductor that amplifies the modulated input signal to produce the amplified signal.

25. A chopper-stabilized analog-to-digital (ADC) converter comprising:

means for modulating an amplitude of an analog input signal at a frequency to produce a modulated input signal;

means for amplifying the modulated input signal to produce an amplified signal, demodulating the amplified signal at the frequency to produce a demodulated signal, and integrating the demodulated signal to produce an output signal;

means for converting the output signal into a digital value that approximates the analog input signal;

means for converting the digital value into a reconstructed analog output signal;

means for modulating an amplitude of the reconstructed analog output signal at the frequency to produce a modulated output signal; and means for applying the modulated output signal as a feedback signal to the modulated input signal.

26. The ADC of claim 25, wherein the modulated input signal is amplified and demodulated prior to any integration of the modulated input signal.

27. The ADC of claim 25, wherein the means for amplifying comprises a transconductor that amplifies the modulated input signal to produce the amplified signal.

28. A method comprising:

modulating an amplitude of an analog input signal at a frequency to produce a modulated input signal;

amplifying the modulated input signal to produce an amplified signal;

demodulating the amplified signal at the frequency to produce a demodulated signal;

integrating the demodulated signal to produce an output signal;

converting the output signal into a digital value that approximates the analog input signal;

converting the digital value into a reconstructed analog output signal;

modulating an amplitude of the reconstructed analog output signal at the frequency to produce a modulated output signal; and applying the modulated output signal as a feedback signal to the modulated input signal via a first feedback path.

29. The method of claim 28, applying the modulated signal to a non-inverting input of a mixer amplifier and applying the modulated feedback signal to an inverting input of the mixer amplifier.

30. The method of claim 28, demodulating the amplified signal comprises demodulating the amplified signal at the frequency to produce a differential output signal.

31. The method of claim 28, wherein the modulated input signal is amplified and demodulated prior to any integration of the modulated input signal.

32. The method of claim 28, wherein amplifying the modulated input signal comprises amplifying the modulated signal with a transconductor.

33. An analog-to-digital converter (ADC) comprising:

a first modulator configured to modulate an amplitude of an input signal at a selected frequency to produce a modulated input signal;

an amplifier configured to amplify the modulated input signal to produce an amplified signal;

a demodulator configured to demodulate an amplitude of the amplified signal at the selected frequency to produce a demodulated signal;

an integrator configured to integrate the demodulated signal to produce an output signal;

circuitry that converts the output signal into a digital value that approximates the analog input signal;

circuitry that converts the digital value into a reconstructed analog output signal;

a second modulator that modulates an amplitude of the reconstructed analog output signal at the selected frequency to produce a modulated output signal; and a feedback path that applies the modulated output signal as a feedback signal to the modulated input signal.

34. The ADC of claim 33, wherein the circuitry that converts the output signal produced by the demodulator into the digital value includes:

a comparator that produces a control signal based on the output signal produced by the demodulator;

a compensator that suppresses the output signal produced by the demodulator at frequencies lower than a high pass corner frequency; and an up/down counter that receives the control signal and increases an amplitude of the digital value when the control signal is received with the first amplitude, and decreases the amplitude of the digital value when the control signal is received with the second amplitude.

35. The ADC of claim 33, wherein the modulated input signal is amplified and demodulated prior to any integration of the modulated input signal.

36. The ADC of claim 33, wherein the amplifier comprises a transconductor that amplifies the modulated input signal to produce the amplified signal.

37. An implantable medical device comprising:

a physiological sensor that generates an input signal indicative of a physiological condition; and an analog-to-digital converter (ADC) comprising:

a first modulator configured to modulate an amplitude of an input signal at a selected frequency to produce a modulated input signal, an amplifier configured to amplify the modulated input signal to produce an amplified signal, a demodulator configured to demodulate an amplitude of the amplified signal at the selected frequency to produce a demodulated signal, an integrator configured to integrate the demodulated signal to produce an output signal, circuitry that converts the output signal into a digital value that approximates the analog input signal, circuitry that converts the digital value into a reconstructed analog output signal, a second modulator that modulates an amplitude of the reconstructed analog output signal at the selected frequency to produce a modulated output signal, and a feedback path that applies the modulated output signal as a feedback signal to the modulated input signal.

38. The device of claim 37, wherein the circuitry that converts the output signal produced by the demodulator into the digital value includes:

a comparator that produces a control signal based on the output signal produced by the demodulator;

an up/down counter that receives the control signal and selectively increases or decreases the digital value based on the control signal.

39. The device of claim 37, wherein the circuitry that converts the output signal produced by the demodulator into the digital value includes a compensator that suppresses the output signal produced by the demodulator at frequencies lower than a high pass corner frequency.

40. The device of claim 37, wherein the sensor includes one of an accelerometer, a pressure sensor, and a voltage sensor.

41. The device of claim 37, wherein the sensor includes one of electrocardiogram (ECG), electromyogram (EMG), or electroencephalogram (EEG) sensor.

42. The device of claim 37, further comprising a processor that controls delivery of a therapy to a patient based on the digital signal from ADC.

43. The device of claim 37, wherein the implantable medical device includes one of a cardiac pacemaker, a cardiac defibrillator, an electrical neurostimulator, and an implantable drug delivery device.

44. The device of claim 37, wherein the modulated input signal is amplified and demodulated prior to any integration of the modulated input signal.

45. The device of claim 37, wherein the amplifier comprises a transconductor that amplifies the modulated input signal to produce the amplified signal.

* * * * *